United States Patent
Yao et al.

(10) Patent No.: US 7,423,198 B2
(45) Date of Patent: Sep. 9, 2008

(54) HIGH OLEIC ACID BRASSICA JUNCEA

(75) Inventors: Kening Yao, Saskatoon (CA); Derek A. Potts, Saskatoon (CA); Daryl R. Males, Saskatoon (CA)

(73) Assignee: Viterra, Inc., Regina (CA)

( * ) Notice: Subject to any disclaimer, the term of this patent is extended or adjusted under 35 U.S.C. 154(b) by 306 days.

(21) Appl. No.: 10/895,520

(22) Filed: Jul. 20, 2004

(65) Prior Publication Data

US 2005/0039233 A1 Feb. 17, 2005

Related U.S. Application Data

(63) Continuation-in-part of application No. 10/330,775, filed on Dec. 26, 2002.

(30) Foreign Application Priority Data

May 15, 2002 (CA) .................................. 2382767
Jul. 15, 2004 (CA) .................................. 2471884

(51) Int. Cl.
*A01H 5/00* (2006.01)
*A01H 5/10* (2006.01)

(52) U.S. Cl. .................................................... 800/306
(58) Field of Classification Search .................. 800/306
See application file for complete search history.

(56) References Cited

U.S. PATENT DOCUMENTS

| | | | |
|---|---|---|---|
| 4,554,101 A | 11/1985 | Hopp | 260/112.5 |
| 5,625,130 A | 4/1997 | Grant et al. | 800/200 |
| 5,668,299 A | 9/1997 | DeBonte et al. | 800/230 |
| 5,840,946 A | 11/1998 | Wong et al. | 554/224 |
| 5,850,026 A | 12/1998 | DeBonte et al. | 800/281 |
| 5,861,187 A | 1/1999 | DeBonte et al. | 426/601 |
| 6,084,157 A | 7/2000 | DeBonte et al. | 800/306 |
| 6,303,849 B1 * | 10/2001 | Potts et al. | 800/306 |

FOREIGN PATENT DOCUMENTS

WO  WO 96/27285  9/1996

OTHER PUBLICATIONS

Poelham et al. 1995. Breeding Field Crops, 4th ed., pp. 108-109.*
Hammond et al. JAOCS 61(11): 1713-1716, 1984.*
Agnihotri, A., Kaushik, N., Singh, N. K., Raney, J. P. and Downey, R. K. 1995. Selection for better agrononical and nutritional characteristics in Indian rapeseed-mustard. Proc. 9.sup. th Int. Rapeseed Cong., Cambridge, U.K. vol. 2:425-427.
Altschul et al., 1990, J. Mol. Biol. 215:403-10.
Ames, B. N. 1983. Dietary carcinogens and anticarcinogens. Science 221:1256-1264.
Ausubel, et al. (eds), 1989, Current Protocols in Molecular Biology, vol. 1, Green Publishing Associates, Inc., and John Wiley & Sons, Inc., New York, at p. 2.10.3.

Daun, J. K. and McGregor, D. I. 1991. Glucosinolates in seeds and residues. In: Analysis of Oilseeds, Fats and Fatty foods. J. B. Rossell and J. L. R. Pritchard, eds. Elsevier Applied Science, London, pp. 185-226.
Downey, R. K. and Rakow, G. F. W. 1987. Rapeseed and mustard. In: Principles of cultivar development. W. R. Fehr, ed. Macmillian, N. Y. pp. 437-486.
Eskin, N. A. M., Vaisey-Genser, M., Durance-Todd, S. and Przybylski, R. 1989. Stability of low linolenic acid canola oil to frying temperatures. J. Amer. Oil Chem. Soc. 66: 1081-1084.
Food Chemicals Codex. 1996. 4.sup. th Edition. Committee on Food Chemicals Codex, Food and Nutrition Board, Institute of Medicine, National Academy of Sciences. National Academy Press, Washington. pp. 77-79.
Griffiths et al., Biochem. J. 252: 641-647, 1988.
Henikoff and Henikoff, 1992, Proc. Natl. Acad. Sci. USA 89: 10915-10919.
Jeong et al., Proceedings of the 3rd National Plant Lipid Cooperative Meeting, 1999. South Lake Tahole, California.
Kirk, J. T. O. and Oram, R. N. 1981. Isolation of erucic acid free lines of *Brassica juncea*: Indian mustard now a potential oilseed crop in Australia. J. Aust. Inst. Agric. Sci. 47:51-52.
Love, H. K., Rakow, G., Raney, J. P. and Downey, R. K. 1990. Development of low glucosinolate mustard. Can. J. Plant Sci. 70:419-424.
Love, H. K., Rakow, G., Raney, J. P. and Downey, R. K. 1991. Breeding improvements towards canola quality *Brassica juncea*. Proc. 8.sup.th Int. Rapeseed Congress, Saskatoon, Canada. vol. 1:164-169.
Marillia and Taylor, Plant Physiol. 120: 339, 1999.
McDonald, B. E. 1995. Oil properties of importance in human nutrition. In: *Brassica* Oilseeds: Production and Utilization. D. S. Kimber and D. I. McGregor, eds., CAB International, Oxon, U.K., pp. 291-299.
Miquel and Browse, J. Bio. Chem. 267: 1502-1509, 1992.
Napoli et al., 1990 Plant Cell 2: 279-289.
Needleman and Wunsch, 1970, J. Mol. Biol. 48:443.
Okuley et al., Plant Cell 6: 147-158,1994.
Pearson and Lipman, 1988, Proc. Natl. Acad. Sci. USA 85: 2444.
Potts and Males. 1999. Inheritance of fatty acid composition in *Brassica juncea*. The proceedings of 10th International Rapeseed Congress in Sep. 26-29, 1999; Canberra, Australia; CD-ROM.

(Continued)

*Primary Examiner*—Medina A. Ibrahim
*Assistant Examiner*—Keith O. Robinson
(74) *Attorney, Agent, or Firm*—Jondle & Associates, P.C.

(57) ABSTRACT

In various aspects, the invention provides *Brassica juncea* plants, seeds, cells, nucleic acid sequences and oils. Edible oil derived from plants of the invention may have significantly higher oleic acid content than other *B. juncea* plants. In one embodiment, the *B. juncea* line MJ02-086-3 contains a mutant allele MJ02-086-3/BjFAD2-a at the BjFAD2-a gene locus, having a premature stop codon, so that there are no functional copies of the FAD2 gene in MJ02-086-3 plants. Seeds from MJ02-086-3 plants may for example yield an oil having oleic acid content of greater than about 70% by weight.

12 Claims, 8 Drawing Sheets

OTHER PUBLICATIONS

Potts et al., 1999. Canola-quality *Brassica juncea*, a new oilseed crop for the Canadian prairies. The Proceedings of 10th International Rapeseed Congress in Sep. 26-29, 1999; Canberra, Australia; CD-ROM.

Rakow, G. 1991. Canola quality mustard. Proc. Special Cropportunities I: A conference organized by the Crop Development Centre and the Extension Division, University of Saskatchewan, Saskatoon, Canada pp. 55-59.

Rakow, G., Raney, J. P. and Males, D. 1995. Field performance of canola quality *Brassica juncea* Proc. 9.sup.th Int. Rapeseed Congress, Cambridge, U.K. vol. 2:428-430.

Raney, P., Rakow, G. and Olson, T. 1995. Development of zero erucic, low linolenic *Brassica juncea* utilizing interspecific crossing. Proc. 9.sup.th Int. Rapeseed Congress, Cambridge, U.K. vol. 2:413-415.

Shanklin and Somerville, Proc. Natl. Acad. Sci. USA 88: 2510-2514, 1991.

Shanklin et al., Biochemistry 33: 12787-12794, 1994.

Singh et al., 1995. Plant Physiol. 109: 1498.

Stotjesdijk et al., 1999. Genetic manipulation for altered oil quality in *Brassica*. The proceedings of 10th International Rapeseed Congress in Sep. 26-29, 1999; Canberra, Australia; CD-ROM.

Swanson, E. B., Coumans, M. P., Brown, G. L., Patel, J. D. and Beversdorf, W. D. 1988. The characterization of herbicide tolerant plants in *Brassica napus* L. after in vitro selection of microspores and protoplasts. Plant Cell Rep. 7:83-87.

Swanson, E. B., Herrgesell, M. J., Amoldo, M., Sippell, D. W. and Wong, R. S. C. 1989. Microspore mutagenesis and selection: canola plants with field tolerance to the imidazolinones. Theor. Appl. Genet. 78:525-530.

Tanhuanpää et al., Mol. Breed. 4: 543-550, 1998.

Thiagarajah, M. R. and Stringham, G. R. 1993. A comparison of genetic segregation in traditional and microspore-derived populations of *Brassica juncea* L. Czem and Coss. Plant Breeding 111:330-334.

Woods, D. L., Capcara, J. J. and Downey, R. K. 1991. The potential of mustard (*Brassica juncea* (L.) Coss) as an edible oil crop on the Canadian Prairies. Can. J. Plant Sci. 71:195-198.

Zhu et al., 1999. Proc. Natl. Acad. Sci. 96: 8768-8773.

Zhu et al., 2000. Nature Biotechnology 18: 555-558.

Smith, Temple. F., et al., "Comparison of Biosequences", *Advances in Applied Mathematics* 2: 482-489 (1981).

Tijssen, "Overview of principles of hybridization and the strategy of nucleic acid probe assays", *Laboratory Techniques in Biochemistry and Molecular Biology—Hybridization with Nucleic Acid Probes*, pp. 19-78 (1993).

Dellaporta, Stephen, L. et al., "A Plant DNA Minipreparation: Version II", *Plant Molecular Biology Reporter* 1: 19-21 (1983).

* cited by examiner

FIGURE 2

```
gatatttttt taagttttttt tctcacatgg gagaagaaga agccaagcac    50
gatcctccat tctcaacttt atagcatttt tttcttttct ttccggctac   100
cactaacttc tacagttcta cttgtgagtc ggcaaggacg tttcctcata   150
ttaaagtaaa gacatcaaat accataatct taatgctaat taacgtaacg   200
gatgagttct ataacacaac ccaaactagt ctttgtgaac attaggattg   250
ggtaaaccaa tatttacatt ttaaaaacaa aatacaaaaa gaaacgtgat   300
aaactttata aaagcaatta tatgatcacg gcatctttt  cactttccg    350
taaatatata taagtggtgt aaatatcaga tatttggagt agaaaaaaaa   400
aaaaaaaaaa agaaatatga agagaggaaa taatggaggg gcccactagt   450
aaaaagaaa  gaaagagat  gtcactcaat cgtctcacac gggcccccgt   500
caatttaaac ggcctgcctt ctgcccaatc gcatcttacc agaaccagag   550
agattcatta ccaaagagat agagagagaa agagaggaga cagagagagt   600
ttgaggaggt gcttcttcgt agggttcatc gttattaacg ttaaatcttc   650
atcccccta  gtcaaccagc tcaaggtccc tttcttcttc catttcctct   700
cattttacg  ttgttttcaa tcttggtctg ttcttttctt atcgcttttc   750
tattctatct atcatttttg cttttcagtc gatttaattc tagacctgtt   800
aatatttatt gcattaaact atagatctgt tcttgattct ctgttttctt   850
gtgtgaaatc ttgatgctgt ctttaccatt aatctgatta tattgtctat   900
accttggaga atatgaaatg ttgcattttc atttgtccga atacaaactg   950
tttgactttc aatctttttt aatgatttat tttgatgggt tggtggagtt  1000
gaaaaatcac catagcagtc tcacgtcctg gtcttagaaa tatccttcct  1050
attcaaagtt atatata ttt gtttacttgt cttagatctg gacctgagac  1100
atgtaagtac ctatttgttg aatctttggg taaaaaactt atgtctctgg  1150
gtaaaatttg cttggagatt tgaccgattc ctattggctc ttgattctgt  1200
aattacgtaa tacatgaaaa atgtttcatt tggcctatgc tcacttcatg  1250
cttataaact ttttcttgca aattaattgg attagatgct ccttcataga  1300
ttcagatgca atagatttgc atgaagaaaa taatagaatt catgatagta  1350
```

FIGURE 2 CONTINUED

```
aaaagattgt attttttgttt gtttgtttat gtttaaaagt ctatatgttg 1400
acaatagagt tgctatcaac tgtttcattt aggtttatgt ttttgtcaag 1450
ttgcttattc taagagacat tgtgattatg acttgtcttc tctaacgtag 1500
tttagtaata aaagacgaaa gaattgata tccacaagaa agagatgtaa 1550
gctgtaacgt atcaaatctc attaataact agtagtattc tcaacgctat 1600
cgtttatttc tttctttggt ttgccactat atgccgcttc tctcctcttt 1650
tgtcccacgt actatccatt tttttgaaac tttaataacg taacactgaa 1700
tattaatttg ttggtttaat taactttgag tttgtttttg gtttatgcag 1750
aaacATGGGT GCAGGTGGAA GAATGCAAGT GTCTCCTCCC TCGAAGAAGT 1800
CTGAAACCGA CACCATCAAG CGCGTACCCT GCGAGACACC GCCCTTCACT 1850
GTCGGAGAAC TCAAGAAAGC AATCCCACCG CACTGTTTCA AACGCTCGAT 1900
CCCTCGCTCT TTCTCCTACC TCATCTGGGA CATCATCATA GCCTCCTGCT 1950
TCTACTACGT CGCCACCACT TACTTCCCTC TCCTCCCTCA CCCTCTCTCC 2000
TACTTCGCCT GGCCTCTCTA CTGGGCCTGC CAGGGCTGCG TCCTAACCGG 2050
CGTCTGGGTC ATAGCCCACG AGTGCGGCCA CCACGCCTTC AGCGACTACC 2100
AGTGGCTTGA CGACACCGTC GGTCTCATCT TCCACTCCTT CCTCCTCGTC 2150
CCTTACTTCT CCTGGAAGTA CAGTCATCGA CGCCACCATT CCAACACTGG 2200
CTCCCTCGAG AGAGACGAAG TGTTTGTCCC CAAGAAGAAG TCAGACATCA 2250
AGTGGTACGG CAAGTACCTC AACAACCCTT TGGGACGCAC CGTGATGTTA 2300
ACGGTTCAGT TCACTCTCGG CTGGCCTTTG TACTTAGCCT TCAACGTCTC 2350
GGGAAGACCT TACGACGGCG GCTTCGCTTG CCATTTCCAC CCTAACGCTC 2400
CCATCTACAA CGACCGCGAG CGTCTCCAGA TATACATCTC CGACGCTGGC 2450
ATCCTCGCCG TCTGCTACGG TCTCTACCGC TACGCTGCTG TCCAAGGAGT 2500
TGCCTCGATG GTCTGCTTCT ACGGAGTCCC GCTTCTGATA GTCAACGGGT 2550
TCTTAGTTTT GATCACTTAC TTGCAGCACA CGCATCCTTC CCTGCCTCAC 2600
```

FIGURE 2 CONTINUED

```
TACGATTCGT CTGAGTGGGA TTGGTTGAGG GGAGCGTTGG CTACCGTTGA 2650
CAGAGACTAC GGGATCTTGA ACAAGGTCTT CCACAATATC ACGGACACGC 2700
ACGTGGCGCA TCACCTGTTC TCGACCATGC CGCATTATCA CGCGATGGAA 2750
GCTACCAAGG CGATAAAGCC GATACTGGGA GAGTATTATC AGTTCGATGG 2800
GACGCCGGTG GTTAAGGCGA TGTGGAGGGA GGCGAAGGAG TGTATCTATG 2850
TGGAACCGGA CAGGCAAGGT GAGAAGAAAG GTGTGTTCTG GTACAACAAT 2900
AAGTTATGA 2909 (SEQ ID NO: 1)
```

FIGURE 3

```
gatatttttt taagtttttt tctcacatgg gagaagaaga agccaagcac    50
gatcctccat tctcaacttt atagcatttt tttctttttct ttccggctac  100
cactaacttc tacagttcta cttgtgagtc ggcaaggacg tttcctcata   150
ttaaagtaaa gacatcaaat accataatct taatgctaat taacgtaacg   200
gatgagttct ataacacaac ccaaactagt ctttgtgaac attaggattg   250
ggtaaaccaa tatttacatt ttaaaacaa aatacaaaaa gaaacgtgat    300
aactttata aagcaatta tatgatcacg gcatctttt cacttttccg      350
taaatatata aagtggtgt aaatatcaga tatttggagt agaaaaaaaa    400
aaaaaaaaaa agaaatatga agagaggaaa taatggaggg gcccactagt   450
aaaaagaaa gaaaagagat gtcactcaat cgtctcacac gggcccccgt    500
caatttaaac ggcctgcctt ctgcccaatc gcatcttacc agaaccagag   550
agattcatta ccaaagagat agagagagaa agagaggaga cagagagagt   600
ttgaggaggt gcttcttcgt agggttcatc gttattaacg ttaaatcttc   650
atcccctac gtcaaccagc tcaaggtccc tttcttcttc catttcctct    700
catttttacg ttgttttcaa tcttggtctg ttctttttctt atcgcttttc  750
tattctatct atcatttttg cttttcagtc gatttaattc tagacctgtt   800
aatatttatt gcattaaact atagatctgt tcttgattct ctgttttctt   850
gtgtgaaatc ttgatgctgt ctttaccatt aatctgatta tattgtctat   900
accttggaga atatgaaatg ttgcattttc atttgtccga atacaaactg   950
tttgactttc aatctttttt aatgatttat tttgatgggt tggtggagtt  1000
gaaaaatcac catagcagtc tcacgtcctg gtcttagaaa tatccttcct  1050
attcaaagtt atatatattt gtttacttgt cttagatctg gacctgagac  1100
atgtaagtac ctatttgttg aatctttggg taaaaaactt atgtctctgg  1150
gtaaaatttg cttggagatt tgaccgattc ctattggctc ttgattctgt  1200
aattacgtaa tacatgaaaa atgtttcatt tggcctatgc tcacttcatg  1250
cttataaact ttttcttgca aattaattgg attagatgct ccttcataga  1300
ttcagatgca atagatttgc atgaagaaaa taatagaatt catgatagta  1350
```

FIGURE 3 CONTINUED

```
aaaagattgt attttTGTTT gtttgtttat gtttaaaagt ctatatgttg 1400
acaatagagt tgctatcaac tgtttcattt aggtttatgt ttttgtcaag 1450
ttgcttattc taagagacat tgtgattatg acttgtcttc tctaacgtag 1500
tttagtaata aaagacgaaa gaaattgata tccacaagaa agagatgtaa 1550
gctgtaacgt atcaaatctc attaataact agtagtattc tcaacgctat 1600
cgtttatttc tttctttggt ttgccactat atgccgcttc tctcctcttt 1650
tgtcccacgt actatccatt tttttgaaac tttaataacg taacactgaa 1700
tattaatttg ttggtttaat taactttgag tttgttttg gtttatgcag 1750
aaacATGGGT GCAGGTGGAA GAATGCAAGT GTCTCCTCCC TCGAAGAAGT 1800
CTGAAACCGA CACCATCAAG CGCGTACCCT GCGAGACACC GCCCTTCACT 1850
GTCGGAGAAC TCAAGAAAGC AATCCCACCG CACTGTTTCA AACGCTCGAT 1900
CCCTCGCTCT TTCTCCTACC TCATCTGGGA CATCATCATA GCCTCCTGCT 1950
TCTACTACGT CGCCACCACT TACTTCCCTC TCCTCCCTCA CCCTCTCTCC 2000
TACTTCGCCT GGCCTCTCTA CTGGGCCTGC CAGGGCTGCG TCCTAACCGG 2050
CGTCTGAGTC ATAGCCCACG AGTGCGGCCA CCACGCCTTC AGCGACTACC 2100
AGTGGCTTGA CGACACCGTC GGTCTCATCT TCCACTCCTT CCTCCTCGTC 2150
CCTTACTTCT CCTGGAAGTA CAGTCATCGA CGCCACCATT CCAACACTGG 2200
CTCCCTCGAG AGAGACGAAG TGTTTGTCCC CAAGAAGAAG TCAGACATCA 2250
AGTGGTACGG CAAGTACCTC AACAACCCTT TGGGACGCAC CGTGATGTTA 2300
ACGGTTCAGT TCACTCTCGG CTGGCCTTTG TACTTAGCCT TCAACGTCTC 2350
GGGAAGACCT TACGACGGCG GCTTCGCTTG CCATTTCCAC CCTAACGCTC 2400
CCATCTACAA CGACCGCGAG CGTCTCCAGA TATACATCTC CGACGCTGGC 2450
ATCCTCGCCG TCTGCTACGG TCTCTACCGC TACGCTGCTG TCCAAGGAGT 2500
TGCCTCGATG GTCTGCTTCT ACGGAGTCCC GCTTCTGATA GTCAACGGGT 2550
TCTTAGTTTT GATCACTTAC TTGCAGCACA CGCATCCTTC CCTGCCTCAC 2600
```

FIGURE 3 CONTINUED

```
TACGATTCGT CTGAGTGGGA TTGGTTGAGG GGAGCGTTGG CTACCGTTGA 2650
CAGAGACTAC GGGATCTTGA ACAAGGTCTT CCACAATATC ACGGACACGC 2700
ACGTGGCGCA TCACCTGTTC TCGACCATGC CGCATTATCA CGCGATGGAA 2750
GCTACCAAGG CGATAAAGCC GATACTGGGA GAGTATTATC AGTTCGATGG 2800
GACGCCGGTG GTTAAGGCGA TGTGGAGGGA GGCGAAGGAG TGTATCTATG 2850
TGGAACCGGA CAGGCAAGGT GAGAAGAAAG GTGTGTTCTG GTACAACAAT 2900
AAGTTATGA 2909 (SEQ ID NO: 2)
```

FIGURE 4

```
J96D-4830    MGAGGRMQVS  PPSKKSETDT  IKRVPCETPP  FTVGELKKAI  40
MJ02-086-3   MGAGGRMQVS  PPSKKSETDT  IKRVPCETPP  FTVGELKKAI  40

J96D-4830    PPHCFKRSIP  RSFSYLIWDI  IIASCFYYVA  TTYFPLLPHP  80
MJ02-086-3   PPHCFKRSIP  RSFSYLIWDI  IIASCFYYVA  TTYFPLLPHP  80

J96D-4830    LSYFAWPLYW  ACQGCVLTGV  WVIAHECGHH  AFSDYQWLDD  120
MJ02-086-3   LSYFAWPLYW  ACQGCVLTGV  *VIAHECGHH  AFSDYQWLDD  120

J96D-4830    TVGLIFHSFL  LVPYFSWKYS  HRRHHSNTGS  LERDEVFVPK  160
MJ02-086-3   TVGLIFHSFL  LVPYFSWKYS  HRRHHSNTGS  LERDEVFVPK  160

J96D-4830    KKSDIKWYGK  YLNNPLGRTV  MLTVQFTLGW  PLYLAFNVSG  200
MJ02-086-3   KKSDIKWYGK  YLNNPLGRTV  MLTVQFTLGW  PLYLAFNVSG  200

J96D-4830    RPYDGGFACH  FHPNAPIYND  RERLQIYISD  AGILAVCYGL  240
MJ02-086-3   RPYDGGFACH  FHPNAPIYND  RERLQIYISD  AGILAVCYGL  240

J96D-4830    YRYAAVQGVA  SMVCFYGVPL  LIVNGFLVLI  TYLQHTHPSL  280
MJ02-086-3   YRYAAVQGVA  SMVCFYGVPL  LIVNGFLVLI  TYLQHTHPSL  280

J96D-4830    PHYDSSEWDW  LRGALATVDR  DYGILNKVFH  NITDTHVAHH  320
MJ02-086-3   PHYDSSEWDW  LRGALATVDR  DYGILNKVFH  NITDTHVAHH  320

J96D-4830    LFSTMPHYHA  MEATKAIKPI  LGEYYQFDGT  PVVKAMWREA  360
MJ02-086-3   LFSTMPHYHA  MEATKAIKPI  LGEYYQFDGT  PVVKAMWREA  360

J96D-4830    KECIYVEPDR  QGEKKGVFWY  NNKL  384  (SEQ ID NO: 7)
MJ02-086-3   KECIYVEPDR  QGEKKGVFWY  NNKL  384  (SEQ ID NO: 8 and 9)
```

HIGH OLEIC ACID BRASSICA JUNCEA

CROSS REFERENCE TO RELATED APPLICATIONS

This is a continuation-in-part of co-pending U.S. patent application Ser. No. 10/330,775, filed Dec. 26, 2002, which is incorporated herein in its entirety.

FIELD OF THE INVENTION

The invention is in the field of improved lines of Brassica, including Brassica juncea, improved oils from Brassica juncea, methods for generation of such lines, and methods for selection of such lines. More specifically certain embodiments relate to Brassica lines with an increased oleic acid content.

BACKGROUND OF THE INVENTION

"Canola" generally refers to plants of Brassica species that have less than 2% erucic acid ($\Delta$13-22:1) by weight in seed oil and less than 30 micromoles of glucosinolates per gram in meal. Typically, canola oil may contain less than about 7% total saturated fatty acids and greater than 60% oleic acid (as percentages of total fatty acids). Traditionally canola crops include Brassica napus and Brassica rapa. Recently, canola quality Brassica juncea, which has oil and meal qualities similar to other canola types, has been added to the canola crop family (U.S. Pat. No. 6,303,849, to Potts et al., issued on Oct. 16, 2001; U.S. Patent Publication No. 20030221217 of 27 Nov. 2003, Yao et al; Potts and Males, 1999; all of which are incorporated herein by reference).

Fatty acid compositions of vegetable oil affect the oil quality and stability. For example, oleic acid has been recognised to have health benefits including effectiveness in lowering plasma cholesterol levels and therefore, higher levels of oleic acid content in seed oil is a desirable trait. Further, not all fatty acids in vegetable oils are equally vulnerable to high temperature and oxidation. Rather, the susceptibility of individual fatty acids to oxidation is dependent on their degree of unsaturation. For example, linolenic acid, which has three carbon-carbon double bonds, is much more vulnerable to oxidation than oleic acid that has only one carbon-carbon double bond. High oleic acid content vegetable oil is also preferred because of its heat stability. For these reasons, high oleic acid and low linolenic acid may be desirable traits in plant oils.

Plants synthesize fatty acids in their plastid as palmitoyl-ACP (16:0-ACP) and stearoyl-ACP. The conversion of stearoyl-ACP to oleoyl-ACP (18:1-ACP) is catalyzed by a soluble enzyme, the stearoyl-ACP $\Delta$9 desaturase (Shaklin and Somerville, 1991). These acyl-ACPs are either used for glycolipid synthesis in chloroplast or transported out of chloroplast into cytoplasm as acyl-CoAs. Further desaturation of oleic acid occurs only after it is used in the synthesis of glycerolipids and incorporated into membranes, which leads to the synthesis of polyunsaturated fatty acids. The synthesis of polyunsaturated fatty acids linoleate ($\Delta$9,12-18:2) and $\alpha$-linolenate ($\Delta$9,12,15-18:3) begins with the conversion of oleic acid ($\Delta$9-18:1) to linoleic acid, the enzymatic step catalyzed by the microsomal $\omega$-6 oleic acid desaturase (FAD2). The linoleic acid is then converted to $\alpha$-linolenic acid through further desaturation by $\omega$-3 linoleic acid desaturase (FAD3). There are reports that manipulation of the FAD2 gene through genetic engineering could alter fatty acid profiles. For example, heterologous expression of a soybean FAD2 gene in an Arabidopsis mutant line led to dramatic increase in the accumulation of polyunsaturated fatty acids (Heppard et al., 1996). In contrast, in a Arabidopsis mutant line fad2-5, where the transcription of FAD2 gene was decreased significantly due to T-DNA insertion, showed a dramatic increase in the accumulation of oleic acid and a significant decrease in the levels of linoleic acid and linolenic acid (Okuley et al., 1994). These findings suggest that the FAD2 gene plays an important role in controlling conversion of oleic acid to linoleic acid in seed storage lipids.

Significant efforts have been made to manipulate the fatty acid profile of plants, particularly oil-seed varieties such as Brassica spp. that are used for the large-scale production of commercial fats and oils (see for example U.S. Pat. No. 5,625, 130 issued 29 Apr. 1997; U.S. Pat. No. 5,668,299 issued 16 Sep. 1997; U.S. Pat. No. 5,767,338 issued 16 Jun. 1998; U.S. Pat. No. 5,840,946 issued 24 Nov. 1998; U.S. Pat. No. 5,850, 026 issued 15 Dec. 1998; U.S. Pat. No. 5,861,187 issued 19 Jan. 1999; U.S. Pat. No. 6,063,947 issued 16 May 2000; U.S. Pat. No. 6,084,157 issued 4 Jul. 2000; U.S. Pat. No. 6,169,190 issued 2 Jan. 2001; U.S. Pat. No. 6,323,392 issued 27 Nov. 2001; and international patent applications WO 97/43907 published 27 Nov. 1997 and WO 00/51415 published 8 Sep. 2000).

Brassica juncea (AB genome) is an amphidiploid plant of the Brassica genus that is generally thought to have resulted from the hybridization of Brassica rapa (A genome) and Brassica nigra (B genome). Brassica napus (AC genome) is also an amphidiploid plant of the Brassica genera but is thought to have resulted from hybridization of Brassica rapa and Brassica oleracea (C genome). Under some growing conditions, B. juncea may have certain superior traits to B. napus. These superior traits may include higher yield, better drought and heat tolerance and better disease resistance. Intensive breeding efforts have produced plants of Brassica species whose seed oil contains less than 2% erucic acid and whose de-fatted meal contains less than 30 micro moles glucosinolates per gram. The term "canola" has been used to describe varieties of Brassica spp. containing low erucic acid ($\Delta^{13}$-22:1) and low glucosinolates. Typically, canola oil may contain less than about 7% total saturated fatty acids and greater than 60% oleic acid (as percentages of total fatty acids). For example, in the U.S., under 21 CFR 184.1555, low erucic acid rapeseed oil derived from Brassica napus or Brassica campestris is recognized as canola oil where it has an erucic acid content of no more than 2% of the component fatty acids (Table I sets out the Food Chemicals Codex (1996) specifications for canola oil). Plant breeders have also selected canola varieties that are low in glucosinolates, such as 3-butenyl, 4-pentenyl, 2-hydroxy-3-butenyl or 2-hydroxy-4-pentenyl glucosinolate. Canola quality meal may for example be defined as having a glucosinolate content of less than 30 micromoles of aliphatic glucosinolates per gram of oil-free meal. Currently, the principle commercial canola crops comprise B. napus and B. rapa (campestris) varieties. U.S. Pat. No. 6,303,849 issued to Potts et al. on 16 Oct. 2001 (incorporated herein by reference) discloses B. juncea lines having an edible oil that has properties similar to canola. The B. juncea lines disclosed therein have a lineage that includes B. juncea lines J90-3450 and J90-4316, deposited as ATCC Accession Nos 203389 and 203390 respectively (both of which were deposited by Agriculture and Agri-Food Canada under the terms of the Budapest Treaty on 23 Oct. 1998 at the American Type Culture Collection, 10801 University Blvd., Manassas, Va. USA 20110-2209).

TABLE A

Food Chemicals Codex (1996) Specifications for Canola Oil

| Property<br>Fatty Acids, % by weight | Canola Oil |
|---|---|
| <14 | <0.1 |
| 14:0 myristic | <0.2 |
| 16:0 palmitic | <6.0 |
| 16:1 | <1.0 |
| 18:0 | <2.5 |
| 18:1 oleic | >50.0 |
| 18:2 linoleic | <40.0 |
| 18:3 linolenic | <14.0 |
| 20:0 | <1.0 |
| 20:1 | <2.0 |
| 22:0 | <0.5 |
| 22:1 erucic | <2.0 |
| 24:0 | <0.2 |
| 24:1 | <0.2 |
| Acid value | <6 |
| Cold Test | Passes test |
| Colour(AOCS-Wesson) | ≦1.5R/15Y |
| Free fatty acids (as oleic) | <0.05% |
| Heavy metals (as Pb) | ≦5 mg/kg |
| Iodine value | 110-126 |
| Lead | <0.1 mg/kg |
| Peroxide value | ≦10 meq/kg |
| Refractive index | 1.465-1.467 |
| Saponifiable value | 178-193 |
| Stability | ≧7 h |
| Sulfur | ≦10 mg/kg |
| Unsaponifiable matter | ≦1.5% |
| Water | ≦0.1% |

SUMMARY OF THE DISCLOSURE

In various aspects, the invention provides *Brassica juncea* plants, seeds, cells, nucleic acid sequences and oils. Edible oil derived from plants of the invention may have significantly higher oleic acid content than other *B. juncea* plants. In one embodiment, the *B. juncea* line MJ02-086-3 contains a mutant allele MJ02-086-3/BjFAD2-a at the BjFAD2-a gene locus, having a premature stop codon, so that there are no functional copies of the FAD2 gene in MJ02-086-3 plants. Seeds from MJ02-086-3 plants may for example yield an oil having oleic acid content of greater than about 70% by weight.

In one aspect of the invention, it has unexpectedly been discovered that the deletion or silencing of all activity of FAD2 enzymes in a *Brassica* plant yields plants capable of producing an oil having oleic acid content of greater than about 70% by weight. Such plants may for example be tetraploid plants or amphidiploid plants, such as *Brassica juncea*, or *B. napus*. In one aspect, the invention accordingly provides for the deletion or silencing of selected FAD2 coding sequences in a plant, such as in lines of *B. juncea* or *B. napus*. Edible oil derived from plants of the invention may be characterised by one or more of the following characteristics: an oleic acid content of at least 70% by weight, a linoleic acid content of less than 25% by weight, a linolenic acid content of less than 14% by weight, a erucic acid content of less than 1% by weight, a palmitic acid content of less than 6% by weight, a stearic acid content of less than 2.5% by weight, and a total saturated fatty acid content of less than 7.1% by weight. In some embodiments, the invention provides low erucic acid oil derived from tetraploid plants having no expressible FAD2 coding sequences, such as *B. juncea* plants, that will meet one or more of the specifications for low erucic acid rapeseed oil in the Food Chemicals Codex, 4th edition (1996), as set out above.

Alternative aspects of the invention include plants and plant parts. As used herein, "plant parts" includes plant cells, seeds, pollen bearing the nucleic acids of the invention or having the FAD2 coding sequences of the invention or having regulatory sequences, such as sequences upstream of FAD2 coding regions, that inhibit expression of all FAD2 coding sequences. Methods are provided for using the plants of the invention, including progeny plants selected by markers of the invention, to obtain plant products. As used herein, "plant products" includes anything derived from a plant of the invention, including plant parts such as seeds, meals, fats or oils, including plant products having altered oleic acid concentrations. Methods are provided for modifying plants so that they have no FAD2 coding sequences capable of expressing an active FAD2 enzyme. Such methods may for example involve inactivating one or more of the FAD2 coding sequences in a plant, so that the plant has no expressible FAD2 coding sequences.

Amplification primers for identifying portions of the FAD2 coding sequences of the invention are provided, which may be used for example to distinguish different alleles of a selected FAD2 locus. Methods are provided for obtaining plants using the FAD2 coding sequences of the invention, or regions upstream of the FAD2 coding sequences of the invention. For example, sequences of the invention may be used to guide or target site-specific mutations that may down-regulate expression of selected FAD2 coding sequences, such as by down-regulating the expression of a FAD2 gene from a selected FAD2 locus or by truncating the FAD2 protein encoded by the FAD2 gene. Classical plant breeding techniques may be used to introduce the FAD2 coding sequences of the invention into progeny of the plants of the invention.

BRIEF DESCRIPTION OF THE DRAWINGS

FIG. 2 shows the nucleotide sequence of the BjFAD2-a gene of the line J96D-4830 (SEQ ID NO:1). The putative upstream non-coding region is shown in lower case and the open reading frame (ORF) is shown in upper case. The potential TATA box of the gene is shown in bold and underlined. The codon TGG in the ORF, which is mutated to TGA in the line MJ02-086-3, is also shown in bold and underlined.

FIG. 3 shows the nucleotide sequence of the BjFAD2-a gene of the line MJ02-086-3 (SEQ ID NO: 2). The putative upstream non-coding region is shown in lower case and ORF is shown in upper case. The potential TATA box is shown in bold and underlined. The codon TGA in the ORF, which is the mutated version from TGG in line J96D-4830, is shown in bold and underlined.

FIG. 4 shows the alignment of the amino acid sequences of the wild type BjFAD2-a protein from line J96D-4830 (SEQ ID NO: 7) and the altered BjFAD2-a protein from line MJ02-086-3 (SEQ iD NOS: 8 and 9). The symbol * denotes the premature translation stop for the protein synthesis caused by codon TGA in the BjFAD2-a gene of line MJ02-086-3.

DETAILED DESCRIPTION

Figure 1:
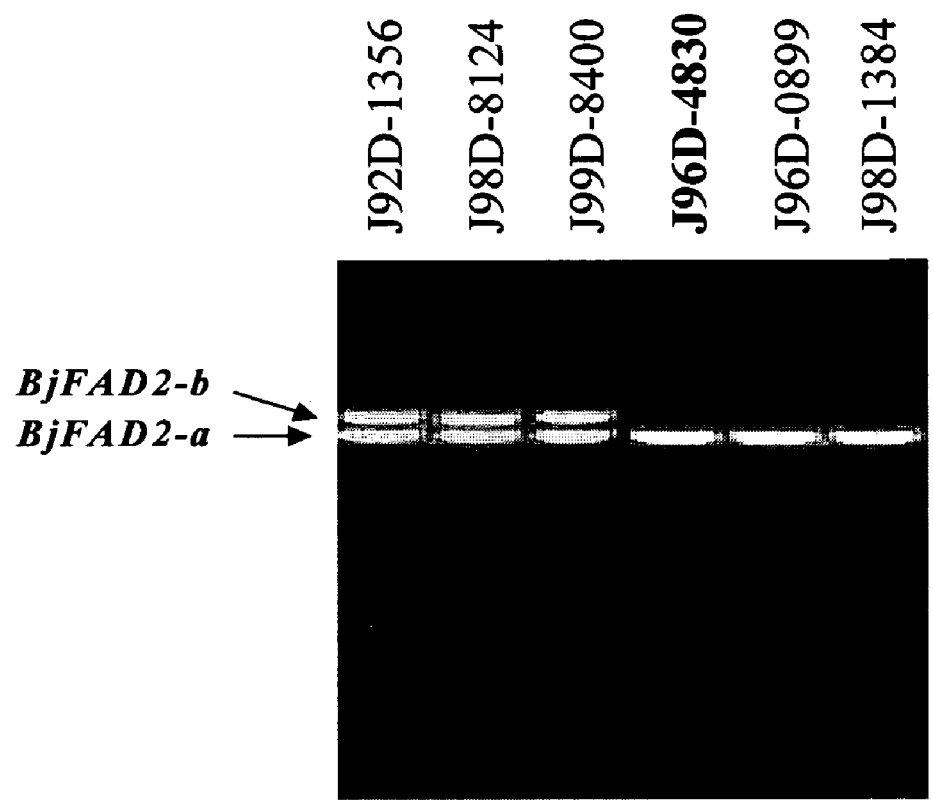
FIG. 1 shows a gel illustrating the results of PCR amplifications of the ω-6 oleate desaturase genes (BjFAD2-b and BjFAD2-a) from various *Brassica juncea* lines using leaf genomic DNA. Three lines are original low erucic acid/low oleic acid *Brassica juncea* (J92D-1356, J96D-3124, J99D-8400); The other three lines are canola quality *Brassica juncea* (J96D-4830, J96D-0899, J98D-1384). PCR amplifications were performed using primers FAD2Pup-1 and FAD2low. Migration positions of the BjFAD2-b and BjFAD2-a genes on the agarose gel after electrophoresis are marked.

For clarity of description, some of the terminology used herein is explained as follows.

The term "line" refers to a group of plants that displays very little overall variation among individuals sharing that designation. A "line" generally refers to a group of plants that display little or no genetic variation between individuals for at least one trait. A "DH (doubled haploid) line", as used in this application refers to a group of plants generated by culturing a haploid tissue and then doubling the chromosome content without accompanying cell division, to yield a plant with the diploid number of chromosomes where each chromosome pair is comprised of two duplicated chromosomes. Therefore, a DH line normally displays little or no genetic variation between individuals for traits.

A "variety" or "cultivar" is a line that is used for commercial production. A "doubled haploid" (DH) line refers to a line created by the process of microspore embryogenesis, in which a plant is created from an individual microspore. By this process, lines are created that are homogeneous, i.e. all plants within the line have the same genetic makeup. The original DH plant is referred to as DH1, while subsequent generations are referred to as DH2, DH3 etc. Doubled haploid procedures are well known and have been established for several crops. A procedure for *B. juncea* has been described by Thiagrarajah and Stringham (1993) (A comparison of genetic segregation in traditional and microspore-derived populations of *Brassica juncea* in: L. Czern and Coss. Plant Breeding 111:330-334).

The term "high oleic" refers to *B. juncea* or other *Brassica* species as the context may dictate, with an oleic acid content higher than that of a wild type or other reference variety or line, most generally it indicates a fatty acid composition comprising at least more than about 55% by weight oleic acid.

"Total saturates" refers to the combined percentages of palmitic (C-16:0), stearic (C-18:0), arachidic (C-20:0), behenic (C-22:0) and tetracosanoic (24:0) fatty acids. The fatty acid concentrations discussed herein are determined in accordance with standard procedures well known to those skilled in the art. Specific procedures are elucidated in the examples. Fatty acid concentrations are expressed as a percentage by weight of the total fatty acid content.

"Halfseed" analysis refers to a procedure whereby fatty acid analysis is carried out on one cotyledon (halfseed) and the remaining halfseed is used to form a plant if the results of the analysis are positive.

"Mutagenesis" is a process in which an agent known to cause mutations in genetic material is applied to plant material. In the experimental work, the mutagenic agent used was ethyl methylsulfonate (EMS). The purpose is to cause new genetic variability in a species usually it is done with a specific trait in mind. An example of mutagenesis used on haploids to induce novel variation has been described by Swanson et al. (Plant Cell Rep. 7:83-87, 1988). The disclosure of this article is herein incorporated by reference. It will be appreciated that a range of other techniques such as recombination with foreign nucleic acid fragments may be suitable to generate mutants and that using certain techniques the generation of mutants may be directed at specific nucleotide or amino acid changes rather than being entirely random. All such methods of introducing nucleic acid sequence changes are understood to be included within the term "mutagenesis" as used herein.

"Regeneration" involves the selection of cells capable of regeneration (e.g. seeds, microspores, ovules, pollen, vegetative parts) from a selected plant or variety. These cells may optionally be subjected to mutagenesis, following which a plant is developed from the cells using regeneration, fertilization, and/or growing techniques based on the types of cells mutagenized. Applicable regeneration techniques are known to those skilled in the art; see, for example, Armstrong, C. L., and Green, C. E., Planta 165:322-332 (1985); and Close, K. R., and Ludeman, L. A., Planta Science 52:81-89 (1987), the disclosures of which are incorporated herein by reference. In this context, "$M_0$" refers to untreated seeds; "$M_1$" refers to the seeds exposed to mutagenis and the resulting plants; "$M_2$" is the progeny (seeds and plants) of self-pollinated $M_1$ plants; "$M_3$" is the progeny (seeds and plants) of self-pollinated $M_2$ plants; "$M_4$" is the progeny (seeds and plants) of self-pollinated $M_3$ plants; "$M_5$" is the progeny (seeds and plants) of self-pollinated $M_4$ plants, and so on.

In this application sequences disclosed may be used to prepare antibodies to the associated proteins, using standard techniques of preparation as, for example, described in Harlow and Lane (Harlow and Lane Antibodies; A Laboratory Manual, Cold Spring Harbor Laboratory, Cold Spring Harbor, N.Y., 1988), or known to those skilled in the art.

For example, a coding sequence for a polypeptide of the invention may be purified to the degree necessary for immunization of rabbits. To attempt to minimize the potential problems of low affinity or specificity of antiserum, two or three polypeptide constructs may be generated for each protein, and each construct is injected into at least two rabbits. Antisera may be raised by injections in a series, preferably including at least three booster injections. Primary immunizations may be carried out with Freund's complete adjuvant and subsequent immunizations with Freund's incomplete adjuvant. Antibody titers may be monitored by Western blot and immunoprecipitation analyses using the purified protein. Immune sera may be affinity purified using CNBr-Sepharose-coupled protein. Antiserum specificity may be determined using a panel of unrelated proteins.

Alternatively or additionally, peptides corresponding to relatively unique immunogenic regions of a polypeptide of the invention may be generated and coupled to keyhole limpet hemocyanin (KLH) through an introduced C-terminal lysine. Antiserum to each of these peptides may be affinity purified on peptides conjugated to BSA, and specificity tested in ELISA and Western blots using peptide conjugates and by Western blot and immunoprecipitation.

Alternatively, monoclonal antibodies which specifically bind any one of the polypeptides of the invention are prepared according to standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981). Once produced, monoclonal antibodies may also be tested for specific recognition by Western blot or immunoprecipitation. Antibodies which specifically bind the polypeptide of the invention are considered to be useful; such antibodies may be used., e.g., in an immunoassay. Alternatively monoclonal antibodies may be prepared using the polypeptide of the invention described above and a phage display library (Vaughan et al., Nature Biotech 14:309-314, 1996).

In some embodiments, antibodies may be produced using polypeptide fragments that appear likely to be immunogenic, by criteria such as high frequency of charged residues. Antibodies can be tailored to minimise adverse host immune response by, for example, using chimeric antibodies contain an antigen binding domain from one species and the Fc portion from another species, or by using antibodies made from hybridomas of the appropriate species.

In some embodiments, antibodies against any of the polypeptides described herein or inferable herefrom may be employed to determine the presence or expression of one of the alleles disclosed and to distinguish between mutated and wild type proteins or other mutants.

In this application "improved characteristics" means that the characteristics in question are altered in a way that is desirable or beneficial or both in comparison with a reference value or attribute, which may relate to the equivalent characteristic of a wild type strain of *Brassica juncea*, or of whichever other *Brassica* line is under consideration. One possible wild type *Brassica juncea* strain whose characteristics may be taken as a reference is J96D-4830 but many others are possible and will readily be identified by those skilled in the art.

In this application "progeny" means the direct and indirect descendants, offspring and derivatives of a plant or plants and includes the first, second, third and subsequent generations and may be produced by self crossing, crossing with plants with the same or different genotypes, and may be modified by range of suitable genetic engineering techniques.

In this application "breeding" includes all methods of developing or propagating plants and includes both intra and inter species and intra and inter line crosses as well as all suitable artificial breeding techniques. Desired traits may be transferred to other *Brassica juncea* lines through conventional breeding methods and can also be transferred to other *Brassica* species, such as *Brassica napus* and *Brassica rapa* through inter-specific crossing. Both conventional breeding methods and inter-specific crossing methods as well as other methods of transferring genetic material between plants are well documented in the literature.

In this application "molecular biological techniques" means all forms of manipulation of a nucleic acid sequence to alter the sequence and expression thereof and includes the insertion, deletion or modification of sequences or sequence fragments and the direct introduction of new sequences into the genome of an organism by directed or random recombination using any suitable vectors and/or techniques.

In this application "genetically derived" as used for example in the phrase "genetically derived from the parent lines" means that the characteristic in question is dictated wholly or in part by an aspect of the genetic makeup of the plant in question.

In this application the term "Brassica" may comprise any or all of the species subsumed in the genus *Brassica* including *Brassica napus, Brassica juncea*, and *Brassica rapa*.

Canola *Brassica juncea* as used in this application refers to *Brassica juncea* that produces seeds with oil and meal quality that meets the requirements for a commercial designation as canola oil or meal, respectively.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny with new combinations of alleles that did not occur in the parental genomes Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

By "substantial homology" is meant a homology of greater than 70%, 71%,72%,73%,74%,75%,76%,77%,78%, 79%,80%,81%,82%,83%,84%,85%, 86%,87%,88%,89%,90%,91%,92%,93%,94%,95%,96%, 97%,98% or 99% up to 100% sequence identity. Homology may refer to nucleic acid or amino acid sequences as the context dictates.

All percentages of fatty acids herein refer to percentage by weight of total fatty acids of oil in which the fatty acid is a component. For example, reference to a plant having a 70% oleic acid content indicates that the fatty acid component of the oil comprises 70% oleic acid.

"Polymorphism" in a population refers to a condition in which the most frequent variant (or allele) of a particular locus has a population frequency which does not exceed 99%.

The term "heterozygosity" (H) is used when a fraction of individuals in a population have different alleles at a particular locus (as opposed to two copies of the same allele). Heterozygosity is the probability that an individual in the population is heterozygous at the locus. Heterozygosity is usually expressed as a percentage (%), ranging from 0 to 100%, or on a scale from 0 to 1.

"Homozygosity" or "homozygous" indicates that a fraction of individuals in a population have two copies of the same allele at a particular locus. Where plants are double haploid it is presumed that subject to any spontaneous mutations occurring during duplication of the haplotype, all loci are homozygous. Plants may be homozygous for one, several or all loci as the context indicates.

"Primers" are short polynucleotides or oligonucleotides required for a polymerase chain reaction that are complementary to a portion of the polynucleotide to be amplified. For example, the primer may be no more than 50 nucleotides long, preferably less than about 30 nucleotides long, and most preferably less than about 24 nucleotides long.

An "isolated" nucleic acid or polynucleotide as used herein refers to a component that is removed from its original environment (for example, its natural environment if it is naturally occurring). An isolated nucleic acid or polypeptide may contain less than about 50%, less than about 75%, less than about 90%, and less than about 99.9% or less than any integer value between 50 and 99.9% of the cellular components with which it was originally associated. A polynucleotide amplified using PCR so that it is sufficiently distinguishable (on a gel from example) from the rest of the cellular components may for example, be considered "isolated". The polynucleotides of the invention may be "substantially pure," i.e., having the highest degree of purity that can be achieved using a particular purification technique known in the art.

"Hybridization" refers to a process in which a strand of nucleic acid joins with a complementary strand through base pairing. Polynucleotides are "hybridizable" to each other when at least one strand of one polynucleotide can anneal to a strand of another polynucleotide under defined stringency conditions. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarily over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarily between the hybridizing sequences. (1×SSC is 0.15 M NaCl, 0.015 M Na citrate.) As used herein, the above solutions and temperatures refer to the probe-washing stage of the hybridization procedure. The term "a polynucleotide that hybridizes under stringent (low, intermediate) conditions" is intended to encompass both single and double-stranded polynucleotides although only one strand will hybridize to the complementary strand of another polynucleotide. Washing in the specified solutions may be conducted for a range of times from several minutes to several days and those skilled in the art will readily select appropriate wash times to discriminate between different levels of homology in bound sequences.

In one aspect, the invention provides Brassica plants, such as Brassica juncea plants, capable of producing seeds having an endogenous fatty acid content comprising a high percentage of oleic acid by weight. Seeds of the invention may also have a low percentage of erucic acid and linoleic acid by weight. In particular embodiments, the oleic acid may comprise more than about 60%, 61%, 62%, 63%, 64%, 65%, 66%, 67%, 68%, 69%, 70%, 71%, 72%, 73%, 74%, 75%, 76%, 77%, 78%, 79% or 80% of the fatty acids, or any integer value greater than 80%. In particular embodiments the erucic acid content of the fatty acids may be less than about 2%, 1.5%,1%, or 0.5%. In particular embodiments the linoleic acid content may be less than about 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11% or 10%. In one exemplary embodiment plant is Brassica juncea, the oleic acid content is greater than 70%, the linoleic acid content is less than about 25% and the erucic acid content is less than 2%.

In selected embodiments, plants of the invention may be Brassica juncea plants of line MJ02-086-3(ATCC Accession No. PTA-6097) or may be progeny plants that are descended from MJ02-086-3plants.

In an alternative aspect, the invention provides methods for increasing the oleic acid content of Brassica plants. Such methods may involve: (a) inducing mutagenesis in at least some cells from a Brassica line that has a oleic acid content >55%; (b) regenerating plants from at least one of said mutagenized cells and selecting regenerated plants which have a fatty acid content comprising at least about 70% oleic acid (or an alternative threshold concentration of oleic acid, as set out above); and (c) deriving further generations of plants from said regenerated plants, individual plants of said further generations of plants having a fatty acid content comprising at least 70% oleic acid (or the alternative threshold concentration). In some embodiments the Brassica may be Brassica juncea. The term "high oleic acid content" encompasses the full range of possible values described above. In alternative embodiments, methods of the invention may further comprise selecting one or more of the lines, the regenerated plants and the further generations of plants for reduced linoleic acid content, such as the range of possible values described above. In further embodiments step (c) may involve selecting and growing seeds from the regenerated plants of step (b). In further embodiments, methods of the invention may comprise repetition of the specified steps until the desired oleic acid content, linoleic acid content, or both, are achieved.

In alternative embodiments, methods are provided for screening individual seeds for increased oleic acid content, and/or decreased linoleic acid content, comprising: determining one or more of the oleic acid content; or the linoleic acid content; or the oleic acid content and the linoleic acid content of the fatty acids of a part of the germinant of the seed; comparing one or more of the contents with a reference value; and inferring the likely relative oleic acid, linoleic acid, or oleic and linoleic acid content of the seed. In particular embodiments the part of the plant used for analysis may be part or all of a leaf, cotyledon, stem, petiole, stalk or any other tissue or fragment of tissue, such as tissues having a composition that demonstrates a reliable correlation with the composition of the seed. In one series of embodiments the part of the germinant may be a part of a leaf. In certain embodiments the step of inferring the fatty acid composition of the seed may comprise assuming that a significantly changed level of a given acid in said leaf reflects a similar relative change in the level of that acid in the seed.

In alternative embodiments the invention provides Brassica plants, which may be Brassica juncea plants, comprising the MJ02-086-3/BjFAD2-a allele at the BjFAD2-a locus. In certain embodiments the plant may be homozygous at the BjFAD2-a locus having the MJ02-086-3/BjFAD2-a allele. In some embodiments, the invention may involve distinguishing canola quality Brassica juncea (~60% oleic acid) from the low erucic/low oleic acid Brassica juncea (~45% oleic acid) by examining the presence or absence of the BjFAD2-b gene (see for reference U.S. patent publication No. 20030221217, Yao et al.). This distinction may involve confirming that the BjFAD2-a gene is the only functional oleate fatty acid desaturase gene in a canola quality Brassica juncea line, such as J96D-4830. In alternative embodiments, the invention provides plants, such as plats of the line MJ02-086-3, having a mutation at the BjFAD2-a gene locus. Aspects of the invention therefore involve the recognition that the MJ02-086-3/BjFAD2-a allele is a mutant allele compared to the J96D-4830/BjFAD2-a wild type allele.

In alternative embodiments, the invention provides nucleic acids, such as isolated or recombinant nucleic acid molecules, comprising the sequence of the MJ02-086-3/BjFAD2-a allele of the invention. Isolated nucleic acids of the invention may include coding sequences of the invention recombined with other sequences, such as cloning vector sequences. Homology to sequences of the invention may be detectable by hybridization with appropriate nucleic acid probes, by PCR techniques with suitable primers or by any other commonly used techniques. In particular embodiments there are provided nucleic acid probes which may comprise sequences homologous to portions of the alleles of the invention. Further embodiments may involve the use of suitable primer pairs to amplify or detect the presence of a sequence of the invention, for example a sequence that is associated with increased oleic acid content.

In selected embodiments, the invention provides isolated DNA sequences comprising complete open reading frames (ORFs) and/or 5' upstream regions of the BjFAD2-a gene, for example from the mutant line MJ02-086-3. For comparison, homologous sequences are disclosed from the wild type line J96D-4830. Comparison of the mutant allele, MJ02-086-3/BjFAD2-a, and the wild type allele, J96D-4830/BjFAD2-a, indicates that the MJ02-086-3/BjFAD2-a allele has a single basepair change (a G to A transition) compared to the corresponding wild type allele J96D-4830/BjFAD2-a, which occurs in the ORF. This single basepair mutation changes the codon TGG (encoding Trp) of the wild type J96D-4830/BjFAD2-a allele to a stop codon TGA in the mutant MJ02-086-3/BjFAD2-a allele. The invention accordingly provides FAD2 coding sequences, such as MJ02-086-3/BjFAD2-a, that encode a non-functional protein, for example due to premature termination during protein translation.

In on aspect of the invention, the mutant MJ02-086-3/BjFAD2-a allele may be used in plant breeding. Specifically, alleles of the invention may be used for breeding high oleic acid *Brassica* species, such as *B. juncea, B. napus, B. rapa, B. nigra* and *B. carinata*. The invention accordingly provides molecular markers for distinguishing mutant alleles, such as the MJ02-086-3/BjFAD2-a allele, form alternative sequences, such as the wild type J96D-4830/BjFAD2-a allele. The invention thereby provides methods for segregation and selection analysis of genetic crosses involving plants having alleles of the invention, such as the MJ02-086-3/BjFAD2-a allele.

In alternative embodiments, the invention provides methods for identifying *Brassica* plants, such as *Brassica juncea* plants, with a desirable fatty acid composition or a desired genomic characteristic. Methods of the invention may for example involve determining the presence in a genome of particular FAD2 alleles, such as the MJ02-086-3/BjFAD2-a allele or the wild type J96D-4830/BjFAD2-a allele. In particular embodiments the methods may comprise identifying the presence of: a nucleic acid polymorphism associated with one of the identified alleles; or an antigenic determinant associated with one of the alleles. Such a determination may for example be achieved with a range of techniques, such as PCR amplification of the relevant DNA fragment, DNA fingerprinting, RNA fingerprinting, gel blotting and RFLP analysis, nuclease protection assays, sequencing of the relevant nucleic acid fragment, the generation of antibodies (monoclonal or polyclonal), or alternative methods adapted to distinguish the protein produced by the relevant alleles from other variants or wild type forms of that protein.

In selected embodiments, the specific single basepair change of the MJ02-086-3/BjFAD2-a mutant allele may be used to design an allele-specific PCR primer, for example making use of a 3' mismatch. Various primer combinations can be made, such as forward primers or reverse primers with a "G/C" at the 3' end (for amplifying that wild type allele) or an "A/T" at the 3' end (for amplifying the mutant allele). For an exemplary summary of allele-specific PCR protocols, see Myakishev et al., 2001, Genome Research 11: 163-169, or Tanhuanpää et al., 1999, Molecular Breeding 4: 543-550.

In alternative embodiments, various methods for detecting single nucleotide polymorphisms (SNPs) may be used for identifying alleles of the invention, such as the MJ02-086-3/BjFAD2-a allele. Such methods may for example include TaqMan assays or Molecular Beacon assays (Täpp et al., BioTechniques 28: 732-738), Invader Assays (Mein et al., Genome Research 10: 330-343, 2000) or assays based on single strand conformational polymorphisms (SSCP) (Orita et al., Proc. Natl. Acad. Sci. U.S.A. 86: 2766-2770, 1989).

In alternative embodiments, the invention provides *Brassica* plants comprising FAD2 coding sequences that encode truncated FAD2 proteins, such as the MJ02-086-3/BjFAD2-a allele or a portion thereof. Such alleles may be selected to be effective to confer an increased oleic acid content on plants of the invention. In particular embodiments, the desired allele may be introduced into plants by breeding techniques. In alternative embodiments, alleles of the invention may be introduced by molecular biological techniques. In such embodiments, the plants of the invention may produce oilseed having an endogenous fatty acid content comprising: at least about 70% oleic acid, or any other oleic acid content threshold as set out above. Plants of the invention may also contain from less than about 25% to less than about 9% linoleic acid, from less than about 14% to less than about 12% linolenic acid, from less than about 2% to less than about 0.2% erucic acid, from less than about 2.5% to less than about 1.6% stearic acid, from less than about 6% to less than about 4% palmitic acid by weight, and have a total fatty acid content of from less than 7.1% to less than about 6.2% by weight and a total glucosinolate content of less than 30 μmole of glucosinolate per gram in oil free meal, wherein the oil composition is genetically derived from the parent line. In one embodiment, the plant produces oilseed having an endogenous fatty acid content comprising at least about 70% of oleic acid, less than 15% of linoleic acid, less than, less than 15% of linolenic acid, less than 0.5% of erucic acid, less than 2.5% stearic acid and less than 4.5% palmitic acid by weight, and have a total saturated fatty acids content of less than 7.1% and a total glucosinolate content of less than 30 μmole of glucosinolate per gram in oil free meal, wherein the oil composition is genetically derived from the parent line.

In alternative embodiments, the invention provides progeny of *Brassica juncea* parent line MJ02-086-3, deposited as ATCC accession number PTA-6097, wherein the progeny produce oilseed having an endogenous fatty acid content comprising the components disclosed in one or more of the foregoing embodiments and wherein the oil composition is genetically derived from the parent line.

In alternative embodiments, the invention provides *Brassica* seed, which may be a *Brassica juncea* seed, having an endogenous fatty acid content having the composition set out for one or more of the foregoing embodiments and wherein the genetic determinants for endogenous oil contend are derived from line MJ02-086-3. Such seed may for example be obtained by self crossing line MJ02-086-3 (ATCC Accession Number PTA-6097), or by crossing MJ02-086-3 with a second parent that is any other *Brassica* line (such as a *B. juncea* line, being a canola quality *B. juncea* or a non-canola quality *B. juncea*, or any other *Brassica* species such as *Brassica napus, B. rapa, B. nigra*, and *B. carinata*.

In alternative embodiments the invention provides genetically stable plants of the genus *Brassica*, such as *Brassica juncea* plants, that develop mature seeds having a composition disclosed in one or more of the foregoing embodiments. Such plants may for example be derived from *B. juncea* MJ-086-3. The oil composition of such plants may be genetically derived from the parent lines.

In alternative embodiments the invention provides processes of producing a genetically stable *Brassica* plant, such as a *B. juncea* I plant, that produces mature seeds having an endogenous fatty acid content comprising the composition specified for one or more of the foregoing embodiments. Processes of the invention may involve the steps of: crossing *B. juncea* MJ02-086-3 with other *Brassica* plants, as described above, to form F1 progeny. The progeny may be propagating, for example by means that may include self pollination or the development of doubled haploid plants. The progeny may be subject to selection for genetically stable plants that generate seeds having a composition disclosed for one or more of the foregoing embodiments. Such seed may for example have a stabilized fatty acid profile that includes a total saturates content of from about 7.1% to about 6.5% in total extractable oils. The stabilized fatty acid profile may be derived from *B. juncea* MJ02-086-3, for example by inheritance of the allele MJ02-086-3/BjFAD2-a. In certain variants the progeny may themselves produce seeds or oil which has a compositions as set out above for alternative embodiments.

In selected embodiments, an increase in oleic acid in plants of the invention, such as plants derived from line MJ02-086-3, may be accompanied by a corresponding decrease in linoleic acid (for example from about 16.72% to about 8.65% in line MJ02-086-3) and a decrease in linolenic acid (for example from 11.97% to 9.41% in line MJ02-086-3), while other fatty acids may remain unchanged.

In some embodiments, FAD2 alleles of the invention may be combined with additional mutant alleles in fatty acid enzymes, such as mutant FAD3 alleles. For example, the MJ02-086-3line may be used to provide FAD2 mutants in crosses with another parent plant with a FAD3 gene mutation.

BjFAD2-a is the only functional FAD2 gene in line J96D-4830. The MJ02-086-3/BjFAD2-a mutant allele abolishes expression of functional FAD2 in line MJ02-086-3. However, line MJ02-086-3has been found to contain a considerable amount of linoleic acid and linolenic acid, which may be synthesized by chloroplast desaturases, such as FAD6 and FAD7, and exported out of chloroplast.

In some embodiments, the stearic acid content may not increase in plants of the invention as a consequence of oleic acid increases. This is for example a characteristic of mutant line MJ02-086-3. In fact, surprisingly, both leaf and seed stearic acid contents are lower in line MJ02-086-3than those in J96D-4830 (Tables 1, 2, 3 and 4). This suggests that in line MJ02-086-3, the sequential conversion of stearic acid to oleic acid, then to linoleic acid and linolenic acid in chloroplast is enhanced, putatively to compensate for the deficiency in FAD2 activity due to the MJ02-086-3/BjFAD2-a allele. Accordingly, in one aspect, the invention provides plants in which there is a decrease in stearic acid export out of chloroplast. In another aspect, the invention provides plants, such as the MJ02-086-3 line and progeny thereof, having lower total saturates than plants that have an active FAD2 gene. In alternative embodiments, other *Brassica* species including *B. juncea, B. napus* and *B. nigra* may be provided with this characteristic.

In one aspect, the invention provides plants have a stable, heritable high oleic acid phenotype. For example, the high oleic acid phenotype resulting from the mutant allele MJ02-086-3/BjFAD2-a in line MJ02-086-3, is genetically heritable through $M_2$ and $M_3$ generations.

In various aspects, the invention involves the modulation of the number of copies of an expressible coding sequence in a plant genome. By "expressible" it is meant that the primary structure, i.e. sequence, of the coding sequence indicates that the sequence encodes an active protein. Expressible coding sequences may nevertheless not be expressed as an active protein in a particular cell. This 'gene silencing' may for example take place by various mechanisms of homologous transgene inactivation in vivo. Homologous transgene inactivation has been described in plants where a transgene has been inserted in the sense orientation, with the unexpected result that both the gene and the transgene were down-regulated (Napoli et al., 1990 Plant Cell 2: 279-289). The exact molecular basis for such co-suppression is unknown, although there are at least two putative mechanisms for inactivation of homologous genetic sequences. Transcriptional inactivation via methylation has been suggested as one mechanism, where duplicated DNA regions signal endogenous mechanisms for gene silencing. A post-transcriptional mechanism has also been suggested, where the combined levels of expression from both the gene and the transgene are thought to produce high levels of transcript which trigger threshold-induced degradation of both messages (van Bokland et al., 1994, Plant J. 6: 861-877). In the present invention, the expressible coding sequences in a genome may accordingly not all be expressed in a particular cell. For example, in some embodiments the FAD2 gene from only one of the two FAD2 loci in the amphidiploid *B. juncea* genome is expressible, and of the two expressible coding sequences at that locus only one may actually be expressed in a particular cell.

In alternative embodiments, the invention provides *Brassica juncea* plants wherein the activity of a fatty acid desaturase is altered or the oleic acid content is altered relative to wild type *B. juncea* (WTBJ). By fatty acid desaturase, it is meant that a protein exhibits the activity of introducing a double bond in the biosynthesis of a fatty acid. For example, FAD2 enzymes may be characterized by the activity of introducing the second double bond in the biosynthesis of linoleic fatty acids (C18:2). Altered desaturase activity may include an increase, reduction or elimination of a desaturase activity compared to a reference plant, cell or sample.

In other aspects, reduction of desaturase activity may include the elimination of expression of a nucleic acid sequence that encodes a desaturase, such as a nucleic acid sequence of the invention. By elimination of expression, it is meant herein that a functional amino acid sequence encoded by the nucleic acid sequence is not produced at a detectable level. Reduction of desaturase activity may include the elimination of transcription of a nucleic acid sequence that encodes a desaturase, such as a sequence of the invention encoding a FAD2 enzyme. By elimination of transcription it is meant herein that the mRNA sequence encoded by the nucleic acid sequence is not transcribed at detectable levels. Reduction of desaturase activity may also include the production of a truncated amino acid sequence from a nucleic acid sequence that encodes a desaturase. By production of a truncated amino acid sequence it is meant herein that the amino acid sequence encoded by the nucleic acid sequence is missing one or more amino acids of the functional amino acid sequence encoded by a wild type nucleic acid sequence. In addition, reduction of desaturase activity may include the production of a variant desaturase amino acid sequence. By production of a variant amino acid sequence it is meant herein that the amino acid sequence has one or more amino acids that are different from the amino acid sequence encoded by a wild type nucleic acid sequence. A variety of mutations may be introduced into a nucleic acid sequence for the purpose of reducing desaturase activity, such as frame-shift mutations, substitutions and deletions. For example, mutations in coding sequences may be made so as to introduce substitutions within functional motifs in a desaturase, such as the motif comprising three-histidine amino residues at amino acids 105-110, 141-145, and 316-320 of FAD2.

In some embodiments, the invention provides new FAD2 polypeptide sequences, which may be modified in accordance with alternative embodiments of the invention. It is well known in the art that some modifications and changes can be made in the structure of a polypeptide without substantially altering the biological function of that peptide, to obtain a biologically equivalent polypeptide. As used herein, the term "conserved amino acid substitutions" refers to the substitution of one amino acid for another at a given location in the peptide, where the substitution can be made without any appreciable loss or gain of function, to obtain a biologically equivalent polypeptide. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Conversely, as used herein, the term "non-conserved amino acid substitutions" refers to the substitution of one amino acid for another at a given location in the peptide, where the substitution causes an appreciable loss or gain of function of the peptide, to obtain a polypeptide that is not biologically equivalent.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). Non-conserved amino acid substitutions may be made were the hydrophilicity value of the residues is significantly different, e.g. differing by more than 2.0. For example, on this basis, the following amino acid substitutions for the wild type His (−0.5) at a position corresponding to amino acid 105 in BjFAD2-b would be non-conserved substitutions: Trp (−3.4), Arg (+3.0); Lys (+3.0); Asp (+3.0); Glu (+3.0).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Non-conserved amino acid substitutions may be made were the hydropathic index of the residues is significantly different, e.g. differing by more than 2.0. For example, on this basis, the following amino acid substitutions for the wild type His (-3.2) at a position corresponding to amino acid 105 in BjFAD2-b would be non-conserved substitutions: Ile (+4.5); Val (+4.2); Leu (+3.8); Phe (+2.8); Cys (+2.5); Met (+1.9); Ala (+1.8); Gly (−0.4); Thr (−0.7); Ser (−0.8); and Trp (−0.9).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Non-conserved amino acid substitutions may be made were the residues do not fall into the same class, for example substitution of a basic amino acid for a neutral or non-polar amino acid.

It is understood that various modifications and alternatives can be made to the present invention. Certain specific embodiments thereof are described in the general methods and further explained by the following examples. The invention certainly applies to all canola quality *B. juncea* species as well as all non-canola quality *B. juncea* species. The invention may be applied to all other *Brassica* species including *B. juncea, B. nigra*, and *B. carinata*, to produce substantially similar results. It should also be understood that the following examples are not intended to limit the invention to particular forms disclosed, but instead, the invention is to cover all modifications, equivalents and alternatives falling within the scope of the invention.

EXAMPLE 1

Creation of a Collection of Mutagenized *B. juncea* Seed Lines

Seeds of *Brassica juncea* line J96D-4830 were selected as the starting material. This line possess an endogenous edible oil with a fatty acid profile identical to that of canola oil, therefore it belongs to the family of canola quality *Brassica juncea* (CQBJ).

The J96D-4830 seeds from several self-pollinated individual plants were pooled and 3000 seeds were subjected to mutagenesis using ethylmethanesulfonate (EMS), a chemical mutagen. More specifically, the seeds were placed in a large petri dish containing 50 ml of 0.3% ethylmethanesulfonate (EMS) water solution. The petri dish was then covered by aluminum foil and incubated at 20° C. for 19 hrs with occasional gentle shaking. At the end of the incubation period, the EMS solution was collected into a bottle and neutralized with $Na_2CO_3$. The EMS treated seeds were washed 5 times with water before being planted into soil (Ready-Earth) in 6 flats, with each flat being divided into 20 rows (25 seeds/row×20 rows/flat=500 seeds/flat). The trays were covered with transparent plastic lids until completion of seed germination. The seeds were geminated in an environmentally controlled greenhouse, which was maintained at 25° C./15° C., 14 hr/10 hr cycles of day/night conditions.

Six days after planting, the germinated seedlings were counted to determine the germination rate. Approximately 1600 out of 3000 EMS treated seeds were germinated to produce M1 plants (53%). All seedlings of these M1 plants were kept in the same greenhouse under the same conditions described above for another 2-3 weeks until the seedlings were transferred individually to 4"×4" pots (Kord Products Inc.). Slow release fertilizer (Brand name) was included in the soil mixture. Due to limited greenhouse space, only 1350 plants were transferred (15 pots/tray×90 trays). The rest of the seedlings were discarded. The transplanted M1 plants were kept in the same growth conditions and bagged individually at flowering for self-pollination. After flowering, the lower leaves of these M1 plants were cut off for easier maintenance and were watered every day until harvesting.

Approximately 680 M1 plants produced M2 seeds. These M2 seeds were harvested from each individual plant, cleaned and packed individually and cataloged. Each M2 seed line has been named systematically as MJ02-001 to MJ02-680, respectively. These M2 seeds were kept under dry and cool conditions until a sub-sample of seeds from each line were planted in greenhouse and leaf tissues were collected from each plant for total fatty acid extraction. Extracted total fatty acids were analyzed for composition profiles by gas liquid chromatography. Detailed screening procedures are described in Example 2.

EXAMPLE 2

Screening for the Increased Oleic Acid Mutant phenotype

After the M2 seeds germinated, leaf tissue of the young seedlings was used for total fatty acid extraction. Analysis by gas liquid chromatography of fatty acid profiles of leaf tissues was used as a primary screening for mutant lines with increased oleic acid content. Although leaf tissue has a very different fatty acid composition than seed, we assume that there is a positive correlation between the two tissues in their fatty acid composition. In the present example, it is demonstrated that in *Brassica juncea*, the oleic acid content in leaves and the oleic acid in seeds may be positively correlated.

Eight seeds from each individual M2 seed line were planted in 2.5"×2.5" soil-containing pots to produce M2 plants. These M2 plants were kept in an environmentally controlled greenhouse having 25° C./15° C., 14 hr/10 hr cycles of day/night conditions. After about 4 weeks when the M2 plants reached 4-5 leaf stages, ~0.1 g of the first leaf from each plant was collected and placed into a plastic vial containing a stainless metal rod (Profast'ners, Saskatoon, Saskatchewan). For total fatty acids extraction, 1 ml of 0.5 M sodium methoxide in methanol (Fisher, Nepean, Ontario) and 0.5 ml of hexane were added to each vial. The vials were capped well and shaken for 10 min at high speed using an Eberback Shaker (Eberback, Ann Arbour, Mich.). After tissue homogenization, the vials were kept at room temperature for an additional 20 min for oil extraction. Then 1 ml of distilled water was added to each vial followed by centrifugation of vials for 5 min at 3500 rpm using a Baxter Canlab Megafuge 1.0 (Heraeus Instruments). After centrifugation, 100 ul of the top hexane layer was transferred into an insert of the auto-sampler vial. Two micro liters of this sample preparation was then injected for analysis of fatty acid composition by gas liquid chromatography (GLC).

The GLC analysis was accomplished with a Hewlett Packard 5890 gas liquid chromatograph equipped with a DB-23 column (0.25-mm inner diameter×30-m length; Hewlett Packard) and a flame ionization detector. For the GLC operation the injector temperature was 250° C. and the detector temperature 300° C. The column temperature was initially held at 160° C. for 0.5 min and gradually increased to 245° C. in a linear gradient fashion at the rate of 10° C./min. The column temperature was then held at 245° C. for additional 4 min. Helium was used as a carrier gas with flow rate of 1 ml/min. The eluted fatty acid methyl esters were integrated and quantified based on area of each peak. The identity of each peak was confirmed by comparison with the following standards (Sigma): palmitic acid (16:0), palmitoleic acid (16:1), stearic acid (18:0), oleic acid (18:1, Δ9), cis-vaccenic acid (18:1, Δ11), linoleic acid (18:2), linolenic acid (18:3), arachidic acid (20:0), cis-11 eicosenoic acid (20:1), cis-11, 14 eicosadinoic acid (20:2), docosanoic acid (22:0), erucic acid (22:1), cis-13, 16 docosadienoic acid (22:2), tetracosanoic acid (24:0) and cis-15 tetracosenoic acid (24:1). Fatty acid profiles were expressed as percentage of individual fatty acid in total identified fatty acids.

In the process of the mutant phenotype screening as such described above, one fatty acid sample, line MJ02-086-3, showed 11.13% oleic acid while the average of control has only 5.5% oleic acid (Table 1). The data also show that there is a corresponding decrease in linoleic acid content in line MJ02-086-3. Other fatty acids remained virtually unchanged. The data shows that the conversion of oleic acid (18:1) to linoleic acid (18:2) is impaired in line MJ02-086-3, suggesting that MJ02-086-3 likely possess a mutation that affected their oleic acid ω-6 desaturase (FAD2) activity.

TABLE 1

Fatty Acid Compositions of Leave Tissues of MJ02-086-3.

| | Composition (%) | |
|---|---|---|
| Fatty Acids | MJ02-086-3 | Average of Control |
| 16:0 | 16.23 | 17.02 |
| 16:1 (cis-9) | 0.21 | 0.23 |
| 18:0 | 2.47 | 2.35 |

TABLE 1-continued

Fatty Acid Compositions of Leave Tissues of MJ02-086-3.

| | Composition (%) | |
|---|---|---|
| Fatty Acids | MJ02-086-3 | Average of Control |
| 18:1 (cis-9) | 11.13 | 5.50 |
| 18:2 (cis-9, 12) | 12.88 | 15.94 |
| 18:3 (cis-9, 12, 15) | 53.45 | 55.65 |
| 20:0 | nd | nd |
| 20:1 | 0.42 | 0.44 |
| 20:2 | 0.20 | 0.25 |
| 22:0 | 0.29 | 0.29 |
| 22:1 (cis-13) | nd | nd |
| 22:2 | 0.96 | 0.53 |
| 24:0 | 0.44 | 0.46 |
| 24:1 | 0.17 | 0.25 |

Note:
The value of the average of control is from multiple data points (n = 40) and the standard deviations of the means for all fatty acids are smaller than 10%.
Nd, indicates non-detectable.

EXAMPLE 3

High Oleic Acid *Brassica juncea* Line

The individual plant MJ02-086-3 (M2) was transferred to a 6" planting pot and bagged before flowering to allow self-pollination and kept in the same growth conditions as described above. There was no abnormal growth and development behavior observed during the entire growth period in respect to leaf size and shape, flowering time, plant height and seed set. After harvesting the seeds (M3), the fatty acid compositions of the seeds were analyzed by gas liquid chromatography in a similar way as for leaf tissue but with modifications in sample preparation. Specifically, for fatty acid extraction, one small scoop of seeds (approximately 300 mg or approximately 80 seeds) was placed into a plastic vial that contains a stainless metal rod (Profast'ners, Saskatoon, Saskatchewan). To each vial, 2 ml of 0.5 M sodium methoxide in methanol (Fisher, Nepean, Ontario) and 1 ml of hexane. The vial was capped well and shaken for 10 min at high speed using an Eberback Shaker (Eberback, Ann Arbour, Mich.). After tissue homogenization, the vials were kept at room temperature for an additional 20 min for oil extraction. Then 1 ml of distilled water was added to each vial followed by centrifugation of vials for 5 min at 3500 rpm using a Baxter Canlab Megafuge 1.0 (Heraeus Instruments). After centrifugation, 100 ul of the top hexane layer was transferred into an auto-sampler vial, to which an additional 400 ul of pure hexane was added. One ul of this sample was then injected for fatty acid composition analysis by gas liquid chromatography (GLC) under the operating conditions described above.

Seed fatty acid analysis results confirmed the high oleic acid phenotype of line MJ02-086-3 (M3) (Table 2). The data show that the oleic acid content in the mutant line MJ02-086-3 is 73.8% compared to ~60% oleic acid content in the original DH line J96D-4830. The data also show that there is a corresponding decrease in linoleic acid in MJ02-086-3. Other fatty acids remain virtually unchanged. Seed fatty acid analysis results confirmed leave tissue fatty acid analysis, which indicated that indeed MJ02-086-3 is a high oleic acid mutant line. Consistency between the results of leaf and seed analysis demonstrates that the method of screening fatty acid composition using leaf tissues to predict fatty acid composition in oilseeds is efficient and accurate. This screening method is better than half seed screening method because its is simple and labor saving. It is also noteworthy that the mutation that causes inactivation/down regulation of FAD2 in line MJ02-086-3is likely recessive. Therefore, the MJ02-086-3 and the following self-pollinated generations are homozygous for the mutant allele. Indeed, when M3 seeds of MJ02-086-3 were again planted in a greenhouse and leaf fatty acids were analyzed from 6 representative M3 individual plants, the results show that all individual plants possess the mutant phenotype, i.e. significantly higher oleic acid content than the wild type line J96D-4830 (Table 3). The data confirmed that MJ02-086-3(M3) was homozygous status for the mutant allele. These individual M3 plants were each bagged to allow self-pollination to produce M4 seeds.

TABLE 2

Seed Fatty Acid Compositions of Mutant Line MJ02-086-3 and the Original Line J96D-4830.

| | Composition (%) | |
|---|---|---|
| Fatty Acid | MJ02-86-3 | J96D-4830 |
| 16:0 | 3.61 | 3.75 |
| 16:1 (cis-9) | 0.30 | 0.21 |
| 18:0 | 1.59 | 2.79 |
| 18:1 (cis-9) | 73.78 | 60.72 |
| 18:2 (cis-9, 12) | 8.65 | 16.72 |
| 18:3 (cis-9, 12, 15) | 9.41 | 11.97 |
| 20:0 | 0.44 | 0.76 |
| 20:1 | 1.25 | 1.43 |
| 20:2 | nd | nd |
| 22:0 | 0.22 | 0.56 |
| 22:1 (cis-13) | nd | nd |
| 22:2 | nd | nd |
| 24:0 | 0.25 | 0.27 |
| 24:1 | 0.38 | 0.46 |

The value of J96D-4830 is an average of 6 independent analysis all showing the similar trend.

TABLE 3

Fatty Acid Compositions of Leaf Tissues from Individual Plants ($M_3$) of the Mutant Line MJ02-086-3.

| | Composition (%) | |
|---|---|---|
| Fatty Acid | MJ02-086-3 ($M_3$) | J96D-4830 |
| 16:0 | 14.07 ± 1.41 | 15.09 ± 0.98 |
| 16:1 (cis-9) | 0.15 ± 0.01 | 0.14 ± 0.11 |
| 18:0 | 1.68 ± 0.02 | 1.95 ± 0.23 |
| 18:1 (cis-9) | 14.04 ± 4.88 | 5.01 ± 0.0 |
| 18:2 (cis-9, 12) | 10.78 ± 3.17 | 15.91 ± 0.01 |
| 18:3 (cis-9, 12, 15) | 58.95 ± 1.43 | 60.05 ± 2.97 |
| 20:0 | 0.12 ± 0.03 | 0.22 ± 0.07 |
| 20:1 | 0.26 ± 0.14 | 0.21 ± 0.15 |
| 20:2 | 0.15 ± 0.02 | 0.16 ± 0.01 |
| 22:0 | 0.18 ± 0.04 | 0.20 ± 0.05 |
| 22:1 (cis-13) | 0.21 ± 0.25 | 0.12 ± 0.17 |
| 22:2 | 0.50 ± 0.36 | 0.54 ± 0.10 |
| 24:0 | 0.43 ± 0.05 | 0.33 ± 0.02 |
| 24:1 | 0.12 ± 0.08 | 0.05 ± 0.07 |

Note:
Leaf tissue samples from MJ02-086-3 individual plant ($M_3$) were analyzed for fatty acid composition.
Values of MJ02-086-3 are means ± SD; n = 6;
Values of J96D-4830 are means ± SD; n = 3.

To illustrate segregation of the mutant gene, the original M2 seeds of MJ02-086 were re-planted in soil in a greenhouse under the same conditions as described above. Leaf tissues were collected from a total of 122 individual plants (M2) for fatty acid composition analysis using the level of oleic acid content as a reference. All individual plants can be categorized into the two groups: high oleic acid individuals (mutant) and low oleic acid individuals (wild type). Table 4 summarizes the analysis result. Using 8% oleic acid content as a cut-off value, 34 individual plants were categorized into mutant group and 88 individuals were categorized into wild type group. As shown in Table 5, the $\chi^2$ for segregation fits the 3:1 Mendelian ratio expected for a single recessive gene mutation.

TABLE 4

Fatty Acid Compositions of Leaf Tissues from $M_2$ Individual Plants of the Mutant Line MJ02-086

| | Mutant (oleic acid >8%) | | | Wild Type (oleic acid <8%) | | |
|---|---|---|---|---|---|---|
| | Composition (%) | | | | | |
| Fatty Acid | Min | Mean | Max | Min | Mean | Max |
| 16:0 | 11.41 | 13.22 | 15.43 | 13.59 | 15.05 | 16.66 |
| 16:1 (cis-9) | 0.12 | 0.13 | 0.16 | 0.10 | 0.14 | 0.28 |
| 18:0 | 1.48 | 1.88 | 2.32 | 1.49 | 2.31 | 2.59 |
| 18:1 (cis-9) | 8.11 | 13.52 | 24.21 | 2.98 | 4.20 | 7.51 |
| 18:2 (cis-9, 12) | 5.02 | 9.65 | 12.81 | 8.93 | 14.78 | 17.24 |
| 18:3 (cis-9, 12, 15) | 51.56 | 57.39 | 62.50 | 54.14 | 59.68 | 64.00 |
| 20:0 | 0.09 | 0.12 | 0.22 | 0.10 | 0.16 | 0.25 |
| 20:1 | 0.15 | 0.30 | 0.61 | 0 | 0.09 | 0.22 |
| 20:2 | 0 | 0.16 | 0.22 | 0.12 | 0.19 | 0.26 |
| 22:0 | 0 | 0.22 | 0.34 | 0 | 0.26 | 1.20 |
| 22:1 (cis-13) | 0 | 0.46 | 1.30 | 0 | 0.43 | 1.54 |
| 22:2 | 1.03 | 1.53 | 2.21 | 0.75 | 1.57 | 2.44 |
| 24:0 | 0.40 | 0.60 | 2.76 | 0.33 | 0.55 | 0.87 |
| 24:1 | 0 | 0.25 | 0.44 | 0 | 0.25 | 0.67 |

Note:
A total of 122 leaf tissue samples from MJ02-086 individual plants ($M_2$) were analyzed for fatty acid composition. Eight percent was used as a cut-off value to distinguish the mutant and the wild type individuals.

TABLE 5

Frequency of Line MJ02-086 $M_2$ Individual Plants with Mutant Fatty Acid and Wild Type Fatty Acid Profiles

| | Wild Type (oleic acid < 8%) | | Mutant (oleic acid > 8%) | | |
|---|---|---|---|---|---|
| Line | Expected | Observed | Expected | Observed | $\chi^2$ (P) |
| MJ02-086 | 91.5 | 88 | 30.5 | 34 | 0.53 (0.47) |

Note:
$\chi^2$ tests are for a single gene (3:1 ratio). Total number of plants tested is 122.

EXAMPLE 4

Genotying of the Mutant Line MJ02-086-3: The Mutant Allele of BjFAD2-α

Breeding line J96D-4830 is a canola *Brassica juncea*. Techniques are available to distinguish canola *Brassica juncea* (~60% oleic acid) from low erucic/low oleic acid *Brassica juncea* (~45% oleic acid) by examining the presence of the BjFAD2-b gene (U.S. Patent Publication No. 20030221217, Yao et al; incorporated herein by reference). Leaf genomic DNA extraction methods and PCR conditions for this analysis are briefly described herein.

Genomic DNA was isolated from leaf tissues as described previously (Dellaporta et al., Plant Mol. Biol. Rep. 1: 19-21, 1983). For direct genomic PCR, 100 ng of genomic DNA was used in total volume of 50 ul containing, 5 μl of 10 × Taq DNA polymerase buffer with $MgCl_2$(Invitrogen) and 2 units of Taq DNA polymerase, 0.25 μM each of primers FAD2Pup-1 (5'-GAAGCCAAGCACGATCCTCCATT-3': SEQ IID NO: 3)

and 2BR4 (5'-ACACGCTTGAGGGTATCGGTTTC-3'; SEQ ID NO: 4) and 50 μM of each dNTP. The amplification was done with 35 cycles of 1 mm at 94° C., 1 mm at 56°C. and 2 mm at 72°C. The PCR products were electrophoresed on 1% agarose gel in TAE running buffer with the 1 Kb plus DNA ladder (BRL) as DNA size marker.

As shown in FIG. 1, using this approach, it was confirmed that both BjFAD2-b and BjFAD2-a genes are present in the original low erucic/low oleic acid *Brassica juncea* lines (J92D-1356, J98D-8124 and J99D-8400). However, the BjFAD2-b gene is missing from the canola *Brassica juncea* lines (J96D-4830, J96D-0889 and J98D-1384).

To identify the mutation in line MJO2-086-3, the whole BjFAD2-a gene was cloned and sequenced from mutant line MJO2-086-3. For this purpose, leaf genomic DNA, isolated from both mutant line MJO2-086-3 and line J96D-4830, were used as PCR template. PCR primers, FAD2Pup (5'-GATATTTTTTAA GTTTTTTTCTCACATGGGAG-3'; SEQ ID NO: 5) and FAD2low (5'-TCATAACTTATTGTTG-TAC CAG-3'; SEQ ID NO: 6), were used to amplify the whole BjFAD2-a gene. For PCR, 100 ng of genomic DNA was used in total volume of 50 ul containing, 5 μl of 10x Taq DNA polymerase buffer with $MgCl_2$ (Invitrogen) and 2 units of Taq DNA polymerase, 0.25 μM each of primers FAD2Pup and FAD2low and 50 μM of each dNTP. The amplification was done with 35 cycles of 1 mm at 94° C., 1 mm at 56° C. and 2 mm at 72° C. The PCR products were electrophoresed on 1% agarose gel in TAE running buffer with the 1 Kb plus DNA ladder (BRL) as DNA size marker. The results show that a single PCR fragment (~2.9 kb in size) was amplified from both lines, which is the expected size of BjFAD2-a gene fragment including the 5' end of the gene promoter and the 3' end of ORF of the BjFAD2-a gene (U.S. patent publication No. 2003/0221217). The PCR fragments were cloned into pDrive cloning vectors (Qiagen Inc. Mississauga Ont.). The inserts were completely sequenced. Comparison of sequences indicated that the BjFAD2-a gene of line MJO2-086-3 is identical to the BjFAD2-a gene of line J96D-4830 except one basepair change, a "G" to "A" transition (FIG. 2 and FIG. 3). The mutation occurs in the ORE of BjFAD2-a gene, where the codon TGG (Tryptophan) of line J96D-4830 became TGA (Stop) in line MJO2-086-3. We designate the mutant allele MJO2-086-3/BjFAD2-a, and the wild type allele J96D-4830/BjFAD2-a. It is obvious that this "G" to "A" transition mutation results in premature stop in protein synthesis (FIG. 4). Accordingly, line MJO2-086-3 has a mutant allele MJO2-086-3/BjFAD2-a at the BjFAD2-a gene locus, conferring increased oleic acid content due to deficiency in oleic acid desaturase activity.

Metabolite analysis shows that in seed the increase in oleic acid in the mutant line MJO2-086-3 is accompanied by a corresponding decrease in linoleic acid (from 16.72% to 8.65%) and a decrease in linolenic acid (from 11.97% to 9.41%). This reflects the fact that the line MJO2-086-3is a FAD2 mutant but not FAD3 mutant. Alternative aspects of the invention provide plants having FAD2 and FAD3 double mutations combined in one line, for example by genetic crosses that are involve MJO2-086-3 as one parent and another parent plant with a FAD3 gene mutation. In some embodiments, FAD2 and FAD3 double mutant lines are provided that are high in oleic acid and low in linolenic acid.

Since the BjFAD2-a is the only functional FAD2 gene locus in line J96D-4830, the MJO2-086-3/BjFAD2-a mutant allele abolishes the expression of functional FAD2 in line MJO2-086-3. However, line MJO2-086-3still contains a considerable amount of linoleic acid and linolenic acid. It is most likely that the considerable amount of linoleic and linolenic acid are synthesized by chloroplast desaturases, putatively FAD6 and FAD7, and exported from the chloroplast.

As evidenced by metabolite analysis, in some embodiments, the stearic acid content of plants of the invention does not increase as oleic acid increases. This is for example the case in line MJO2-086-3. Surprisingly, both leaf and seed stearic acid contents are lower in line MJO2-086-3than those in J96D-4830 (Tables 1, 2, 3 and 4). Accordingly, in one aspect the invention provides plants, such as *Brassica juncea* line MJO2-086-3, that have lower total saturates than wild type plants.

A deposit of the Saskatchewan Wheat Pool, Inc. proprietary *Brassica juncea* line MJO2-086-3 disclosed above and recited in the appended claims has been made with the American Type Culture Collection (ATCC), 10801 University Boulevard, Manassas, Va. 20110. The date of deposit was Jun. 22, 2004. The deposit of 2,500 seeds was taken from the same deposit maintained by Saskatchewan Wheat Pool, Inc. since prior to the filing date of this application. All restrictions upon the deposit have been removed, and the deposit is intended to meet all of the requirements of 37 C.F.R. 1.801-1.809. The ATCC accession number is PTA-6097. The deposit will be maintained in the depository for a period of 30 years, or 5 years after the last request, or for the effective life of the patent, whichever is longer, and will be replaced as necessary during that period.

REFERENCES

The following documents are specifically incorporated herein by reference.

Agnihotri, A., Kaushik, N., Singh, N. K., Raney, J. P. and Downey, R. K. 1995. Selection for better agrononical and nutritional characteristics in Indian rapeseed-mustard. Proc. 9th Int. Rapeseed Cong., Cambridge, U.K. Vol. 2:425-427.

Ames, B. N. 1983. Dietary carcinogens and anticarcinogens. Science 221:1256-1264.

Daun, J. K. and McGregor, D. I. 1991. Glucosinolates in seeds and residues. In: Analysis of Oilseeds, Fats and Fatty foods. J. B. Rossell and J. L. R. Pritchard, eds. Elsevier Applied Science, London, pp. 185-226.

Downey, R. K. and Rakow, G. F. W. 1987. Rapeseed and mustard. In: Principles of cultivar development. W. R. Fehr, ed. Macmillian, N.Y. Pp. 437-486.

Eskin, N. A. M., Vaisey-Genser, M., Durance-Todd, S. and Przybylski, R. 1989. Stability of low linolenic acid canola oil to frying temperatures. J. Amer. Oil Chem. Soc. 66: 1081-1084.

Food Chemicals Codex. 1996. 4. sup.th Edition. Committee on Food Chemicals Codex, Food and Nutrition Board, Institute of Medicine, National Academy of Sciences. National Academy Press, Washington. pp. 77-79.

Kirk, J. T. 0. and Oram, R. N. 1981. Isolation of erucic acid free lines of *Brassica juncea*: Indian mustard now a potential oilseed crop in Australia. J. Aust. Inst. Agric. Sci. 47:51-52.

Love, H. K., Rakow, G., Raney, J. P. and Downey, R. K. 1990. Development of low glucosinolate mustard. Can. J. Plant Sci. 70:419-424.

Love, H. K., Rakow, G., Raney, J. P. and Downey, R. K. 1991. Breeding improvements towards canola quality *Brassica juncea*. Proc. 8. sup.th Int. Rapeseed Congress, Saskatoon, Canada. Vol. 1:164-169.

McDonald, B. E. 1995. Oil properties of importance in human nutrition. In: *Brassica* Oilseeds: Production and Utilization. D. S. Kimber and D. I. McGregor, eds., CAB International, Oxon, U.K., pp. 291-299.

Potts et al., 1999. Canola-quality *Brassica juncea*, a new oilseed crop for the Canadian prairies. The proceedings of 10th International Rapeseed Congress in Sep. 26-29, 1999; Canberra, Australia; CD-ROM.

Potts and Males. 1999. Inheritance of fatty acid composition in *Brassica juncea*. The proceedings of 10th International Rapeseed Congress in Sep. 26-29, 1999; Canberra, Australia; CD-ROM.

Rakow, G. 1991. Canola quality mustard. Proc. Special Cropportunities I: A conference organized by the Crop Development Centre and the Extension Division, University of Saskatchewan, Saskatoon, Canada pp. 55-59.

Rakow, G., Raney, J. P. and Males, D. 1995. Field performance of canola quality *Brassica juncea* Proc. 9. sup.th Int. Rapeseed Congress, Cambridge, U.K. Vol. 2:428-430.

Raney, P., Rakow, G. and Olson, T. 1995. Development of zero erucic, low linolenic *Brassica juncea* utilizing interspecific crossing. Proc. 9. sup.th Int. Rapeseed Congress, Cambridge, U.K. Vol. 2:413-415.

Stotjesdijk et al., 1999. Genetic manipulation for altered oil quality in *Brassica*. The proceedings of 10th International Rapeseed Congress in Sep. 26-29, 1999; Canberra, Australia; CD-ROM.

Swanson, E. B., Coumans, M. P., Brown, G. L., Patel, J. D. and Beversdorf, W. D. 1988. The characterization of herbicide tolerant plants in *Brassica napus* L. after in vitro selection of microspores and protoplasts. Plant Cell Rep. 7:83-87.

Swanson, E. B., Herrgesell, M. J., Arnoldo, M., Sippell, D. W. and Wong, R. S. C. 1989. Microspore mutagenesis and selection: canola plants with field tolerance to the imidazolinones. Theor. Appl. Genet. 78:525-530.

Thiagarajah, M. R. and Stringham, G. R. 1993. A comparison of genetic segregation in traditional and microspore-derived populations of *Brassica juncea* L. Czem and Coss. Plant Breeding 111:330-334.

Woods, D. L., Capcara, J. J. and Downey, R. K. 1991. The potential of mustard (*Brassica juncea* (L.) Coss) as an edible oil crop on the Canadian Prairies. Can. J. Plant Sci. 71:195-198.

CONCLUSION

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

The invention claimed is:

1. A *Brassica juncea* plant whose seeds have an endogenous fatty acid content comprising at least about 70% oleic acid by weight and less than 2% erucic acid by weight wherein said seed has been deposited under ATCC Accession No. PTA-6097.

2. A *Brassica juncea* plant whose seeds have an endogenous fatty acid content comprising less than 25% linoleic acid by weight and less than 2% erucic acid by weight wherein said seed has been deposited under ATCC Accession No. PTA-6097.

3. The *Brassica juncea* plant according to any one of claims 1 and 2 wherein the oleic acid content of said endogenous fatty acid content is at least 73% by weight, wherein said seed has been deposited under ATCC Accession No. PTA-6097.

4. A *Brassica juncea* plant or a part thereof containing the MJ02-086-3/BjFAD2-a mutant allele having the nucleic acid sequence of SEQ ID NO: 2, wherein a representative sample of seed of said plant or a part thereof have been deposited under ATCC Accession No. PTA-6097.

5. The *Brassica juncea* plant or a part thereof according to claim 4 wherein said plant is homozygous for a locus represented by MJ02-086-3/BjFAD2-a mutant allele.

6. The plant of claim 4 wherein said mutant allele confers an increased oleic acid content.

7. The plant or a part thereof according to claim 6, wherein said allele is introduced into said plant or a part thereof by breeding.

8. The plant or a part thereof according to claim 6, wherein the plant or a part thereof produces oilseed having an endogenous fatty acid content comprising:

(a) at least 70% of oleic acid,
(b) less than 25% Linoleic acid,
(c) less than 14% linolenic acid,
(d) less than 2% erucic acid,
(e) less than 2.5% stearic acid,
(f) less than 6% palmitic acid by weight, and having a total fatty acid content of less than 7.1% by weight, wherein the oil composition is genetically derived from the parent line.

9. A *Brassica juncea* seed of line MJ02-086-3 having an endogenous fatty acid content comprising:

(a) at least 70% of oleic acid,
(b) less than 25% Linoleic acid,
(c) less than 14% linolenic acid,
(d) less than 2% erucic acid,
(e) less than 2.5% stearic acid,
(f) less than 6% palmitic acid by weight, and having a total fatty acid content of less than 7.1% by weight, wherein a representative sample of seed have been deposited under ATCC Accession Number PTA-6097.

10. A *Brassica juncea* seed designated MJ02-086-3, representative sample of seed have been deposited under ATCC Accession No. PTA-6097.

11. A *Brassica juncea* plant produced by growing the seed of claim 9.

12. A *Brassica juncea* plant produced by growing the seed of claim 10.

* * * * *

SEQUENCE LISTING

<160> NUMBER OF SEQ ID NOS: 9

<210> SEQ ID NO 1
<211> LENGTH: 2909
<212> TYPE: DNA
<213> ORGANISM: Brassica juncea

<400> SEQUENCE: 1

```
gatattttt  taagtttttt  tctcacatgg  gagaagaaga  agccaagcac  gatcctccat      60
tctcaacttt  atagcatttt  tttcttttct  ttccggctac  cactaacttc  tacagttcta     120
cttgtgagtc  ggcaaggacg  tttcctcata  ttaaagtaaa  gacatcaaat  accataatct     180
taatgctaat  taacgtaacg  gatgagttct  ataacacaac  ccaaactagt  ctttgtgaac     240
attaggattg  ggtaaaccaa  tatttacatt  ttaaaaacaa  aatacaaaaa  gaaacgtgat     300
aaactttata  aaagcaatta  tatgatcacg  gcatcttttt  cacttttccg  taaatatata     360
taagtggtgt  aaatatcaga  tatttggagt  agaaaaaaaa  aaaaaaaaaa  agaaatatga     420
agagaggaaa  taatggaggg  gcccactagt  aaaaaagaaa  gaaaagagat  gtcactcaat     480
cgtctcacac  gggccccgt   caatttaaac  ggcctgcctt  ctgcccaatc  gcatcttacc     540
agaaccagag  agattcatta  ccaaagagat  agagagagaa  agagaggaga  cagagagagt     600
ttgaggaggt  gcttcttcgt  agggttcatc  gttattaacg  ttaaatcttc  atcccctac      660
```

```
gtcaaccagc tcaaggtccc tttcttcttc catttcctct cattttttacg ttgttttcaa      720 tcttggtctg ttcttttctt atcgcttttc tattctatct atcattttg cttttcagtc       780 gatttaattc tagacctgtt aatatttatt gcattaaact atagatctgt tcttgattct       840
ctgttttctt gtgtgaaatc ttgatgctgt ctttaccatt aatctgatta tattgtctat      900
accttggaga atatgaaatg ttgcattttc atttgtccga atacaaactg tttgactttc       960 aatcttttt aatgatttat tttgatgggt tggtggagtt gaaaaatcac catagcagtc      1020
tcacgtcctg gtcttagaaa tatccttcct attcaaagtt atatatattt gtttacttgt     1080
cttagatctg gacctgagac atgtaagtac ctatttgttg aatctttggg taaaaaactt     1140
atgtctctgg gtaaaatttg cttggagatt tgaccgattc ctattggctc ttgattctgt     1200
aattacgtaa tacatgaaaa atgtttcatt tggcctatgc tcacttcatg cttataaact     1260
ttttcttgca aattaattgg attagatgct ccttcataga ttcagatgca atagatttgc     1320
atgaagaaaa aatagaatt catgatagta aaaagattgt attttttgttt gtttgtttat     1380 gtttaaaagt ctatatgttg acaatagagt tgctatcaac tgtttcattt aggtttatgt     1440
ttttgtcaag ttgcttattc taagagacat tgtgattatg acttgtcttc tctaacgtag     1500
tttagtaata aaagacgaaa gaaattgata tccacaagaa agagatgtaa gctgtaacgt     1560
atcaaatctc attaataact agtagtattc tcaacgctat cgtttatttc tttctttggt     1620
ttgccactat atgccgcttc tctcctcttt tgtcccacgt actatccatt tttttgaaac     1680
tttaataacg taaacactgaa tattaatttg ttggtttaat taactttgag tttgtttttg     1740
gtttatgcag aaacatgggt gcaggtggaa gaatgcaagt gtctcctccc tcgaagaagt     1800
ctgaaaccga caccatcaag cgcgtaccct gcgagacacc gcccttcact gtcggagaac     1860
tcaagaaagc aatcccaccg cactgtttca aacgctcgat ccctcgctct ttctcctacc     1920
tcatctggga catcatcata gcctcctgct tctactacgt cgccaccact tacttccctc     1980
tcctccctca ccctctctcc tacttcgcct ggcctctcta ctgggcctgc cagggctgcg     2040
tcctaaccgg cgtctgggtc atagcccacg agtgcggcca ccacgccttc agcgactacc     2100
agtggcttga cgacaccgtc ggtctcatct tccactcctt cctcctcgtc ccttacttct     2160
cctggaagta cagtcatcga cgccaccatt ccaacactgg ctccctcgag agagacgaag     2220
tgtttgtccc caagaagaag tcagacatca agtggtacgg caagtacctc aacaacccctt     2280 tgggacgcac cgtgatgtta acggttcagt tcactctcgg ctggcctttg tacttagcct     2340
tcaacgtctc gggaagacct tacgacggcg gcttcgcttg ccatttccac cctaacgctc     2400
ccatctacaa cgaccgcgag cgtctccaga tatacatctc cgacgctggc atcctcgccg     2460
tctgctacgg tctctaccgc tacgctgctg tccaaggagt tgcctcgatg gtctgcttct     2520
acggagtccc gcttctgata gtcaacgggt tcttagtttt gatcacttac ttgcagcaca     2580
cgcatccttc cctgcctcac tacgattcgt ctgagtggga ttggttgagg ggagcgttgg     2640
ctaccgttga cagagactac gggatcttga acaaggtctt ccacaatatc acggacacgc     2700
acgtggcgca tcacctgttc tcgaccatgc cgcattatca cgcgatggaa gctaccaagg     2760
cgataaagcc gatactggga gagtattatc agttcgatgg gacgccggtg gttaaggcga     2820
tgtggaggga ggcgaaggag tgtatctatg tggaaccgga caggcaaggt gagaagaaag     2880
gtgtgttctg gtacaacaat aagttatga                                       2909
```

<210> SEQ ID NO 2
<211> LENGTH: 2909

<212> TYPE: DNA
<213> ORGANISM: Brassica juncea

<400> SEQUENCE: 2

| | | | | | |
|---|---|---|---|---|---|
| gatatttttt | taagtttttt | tctcacatgg | gagaagaaga | agccaagcac | gatcctccat | 60 |
| tctcaactt | atagcattt | tttcttttct | ttccggctac | cactaacttc | tacagttcta | 120 |
| cttgtgagtc | ggcaaggacg | tttcctcata | ttaaagtaaa | gacatcaaat | accataatct | 180 |
| taatgctaat | taacgtaacg | gatgagttct | ataacacaac | ccaaactagt | ctttgtgaac | 240 |
| attaggattg | ggtaaaccaa | tatttacatt | ttaaaaacaa | atacaaaaa | gaaacgtgat | 300 |
| aaactttata | aaagcaatta | tatgatcacg | gcatcttttt | cacttttccg | taaatatata | 360 |
| taagtggtgt | aaatatcaga | tatttggagt | agaaaaaaaa | aaaaaaaaaa | agaaatatga | 420 |
| agagaggaaa | taatggaggg | gcccactagt | aaaaagaaa | gaaagagat | gtcactcaat | 480 |
| cgtctcacac | gggcccccgt | caatttaaac | ggcctgcctt | ctgcccaatc | gcatcttacc | 540 |
| agaaccagag | agattcatta | ccaaagagat | agagagagaa | agagaggaga | cagagagagt | 600 |
| ttgaggaggt | gcttcttcgt | agggttcatc | gttattaacg | ttaaatcttc | atcccctac | 660 |
| gtcaaccagc | tcaaggtccc | tttcttcttc | catttcctct | cattttacg | ttgttttcaa | 720 |
| tcttggtctg | ttcttttctt | atcgcttttc | tattctatct | atcattttg | cttttcagtc | 780 |
| gattaattc | tagacctgtt | aatatttatt | gcattaaact | atagatctgt | tcttgattct | 840 |
| ctgttttctt | gtgtgaaatc | ttgatgctgt | ctttaccatt | aatctgatta | tattgtctat | 900 |
| accttggaga | atatgaaatg | ttgcatttc | atttgtccga | atacaaactg | tttgactttc | 960 |
| aatctttttt | aatgatttat | tttgatgggt | tggtggagtt | gaaaaatcac | catagcagtc | 1020 |
| tcacgtcctg | gtcttagaaa | tatccttcct | attcaaagtt | atatatattt | gtttacttgt | 1080 |
| cttagatctg | gacctgagac | atgtaagtac | ctatttgttg | aatctttggg | taaaaaactt | 1140 |
| atgtctctgg | gtaaaatttg | cttggagatt | tgaccgattc | ctattggctc | ttgattctgt | 1200 |
| aattacgtaa | tacatgaaaa | atgtttcatt | tggcctatgc | tcacttcatg | cttataaact | 1260 |
| ttttcttgca | aattaattgg | attagatgct | ccttcataga | ttcagatgca | atagatttgc | 1320 |
| atgaagaaaa | taatagaatt | catgatagta | aaaagattgt | attttgttt | gtttgtttat | 1380 |
| gtttaaaagt | ctatatgttg | acaatagagt | tgctatcaac | tgtttcattt | aggtttatgt | 1440 |
| ttttgtcaag | ttgcttattc | taagagacat | tgtgattatg | acttgtcttc | tctaacgtag | 1500 |
| tttagtaata | aaagacgaaa | gaaattgata | tccacaagaa | agagatgtaa | gctgtaacgt | 1560 |
| atcaaatctc | attaataact | agtagtattc | tcaacgctat | cgtttattc | tttctttggt | 1620 |
| ttgccactat | atgccgcttc | tctcctcttt | tgtcccacgt | actatccatt | ttttgaaac | 1680 |
| tttaataacg | taacactgaa | tattaatttg | ttggtttaat | taactttgag | tttgtttttg | 1740 |
| gtttatgcag | aaacatgggt | gcaggtggaa | gaatgcaagt | gtctcctccc | tcgaagaagt | 1800 |
| ctgaaaccga | caccatcaag | cgcgtaccct | gcgagacacc | gcccttcact | gtcggagaac | 1860 |
| tcaagaaagc | aatcccaccg | cactgtttca | aacgctcgat | ccctcgctct | ttctcctacc | 1920 |
| tcatctggga | catcatcata | gcctcctgct | tctactacgt | cgccaccact | tacttccctc | 1980 |
| tcctccctca | ccctctctcc | tacttcgcct | ggcctctcta | ctgggcctgc | cagggctgcg | 2040 |
| tcctaaccgg | cgtctgagtc | atagcccacg | agtgcggcca | ccacgccttc | agcgactacc | 2100 |
| agtggcttga | cgacaccgtc | ggtctcatct | tccactcctt | cctcctcgtc | ccttacttct | 2160 |
| cctggaagta | cagtcatcga | cgccaccatt | ccaacactgg | ctccctcgag | agagacgaag | 2220 |

-continued

```
tgtttgtccc caagaagaag tcagacatca agtggtacgg caagtacctc aacaacccTt    2280
tgggacgcac cgtgatgtta acggttcagt tcactctcgg ctggcctttg tacttagcct    2340
tcaacgtctc gggaagacct tacgacggcg gcttcgcttg ccatttccac cctaacgctc    2400
ccatctacaa cgaccgcgag cgtctccaga tatacatctc cgacgctggc atcctcgccg    2460
tctgctacgg tctctaccgc tacgctgctg tccaaggagt tgcctcgatg gtctgcttct    2520
acggagtccc gcttctgata gtcaacgggt tcttagtttt gatcacttac ttgcagcaca    2580
cgcatccttc cctgcctcac tacgattcgt ctgagtggga ttggttgagg ggagcgttgg    2640
ctaccgttga cagagactac gggatcttga acaaggtctt ccacaatatc acggacacgc    2700
acgtggcgca tcacctgttc tcgaccatgc cgcattatca cgcgatggaa gctaccaagg    2760
cgataaagcc gatactggga gagtattatc agttcgatgg gacgccggtg gttaaggcga    2820
tgtggaggga ggcgaaggag tgtatctatg tggaaccgga caggcaaggt gagaagaaag    2880
gtgtgttctg gtacaacaat aagttatga                                      2909
```

```
<210> SEQ ID NO 3
<211> LENGTH: 23
<212> TYPE: DNA
<213> ORGANISM: Artificial
<220> FEATURE:
<223> OTHER INFORMATION: Primer: FAD2Pup-1

<400> SEQUENCE: 3
gaagccaagc acgatcctcc att                                              23

<210> SEQ ID NO 4
<211> LENGTH: 23
<212> TYPE: DNA
<213> ORGANISM: Artificial
<220> FEATURE:
<223> OTHER INFORMATION: Primer: 2BR4

<400> SEQUENCE: 4
acacgcttga gggtatcggt ttc                                              23

<210> SEQ ID NO 5
<211> LENGTH: 33
<212> TYPE: DNA
<213> ORGANISM: Artificial
<220> FEATURE:
<223> OTHER INFORMATION: Primer: FAD2Pup

<400> SEQUENCE: 5
gatatttttt taagtttttt tctcacatgg gag                                   33

<210> SEQ ID NO 6
<211> LENGTH: 22
<212> TYPE: DNA
<213> ORGANISM: Artificial
<220> FEATURE:
<223> OTHER INFORMATION: Primer: FAD2low

<400> SEQUENCE: 6
tcataactta ttgttgtacc ag                                               22

<210> SEQ ID NO 7
<211> LENGTH: 384
<212> TYPE: PRT
<213> ORGANISM: Brassica juncea

<400> SEQUENCE: 7
```

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
                180                 185                 190

Tyr Leu Ala Phe Asn Val Ser Gly Arg Pro Tyr Asp Gly Gly Phe Ala
            195                 200                 205

Cys His Phe His Pro Asn Ala Pro Ile Tyr Asn Asp Arg Glu Arg Leu
            210                 215                 220

Gln Ile Tyr Ile Ser Asp Ala Gly Ile Leu Ala Val Cys Tyr Gly Leu
225                 230                 235                 240

Tyr Arg Tyr Ala Ala Val Gln Gly Val Ala Ser Met Val Cys Phe Tyr
                245                 250                 255

Gly Val Pro Leu Leu Ile Val Asn Gly Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Ala Thr Lys Ala
                325                 330                 335

Ile Lys Pro Ile Leu Gly Glu Tyr Tyr Gln Phe Asp Gly Thr Pro Val
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
            370                 375                 380

<210> SEQ ID NO 8
<211> LENGTH: 100
<212> TYPE: PRT
<213> ORGANISM: Brassica juncea
```

<400> SEQUENCE: 8

```
Met Gly Ala Gly Gly Arg Met Gln Val Ser Pro Ser Lys Lys Ser
1               5                   10                  15

Glu Thr Asp Thr Ile Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Ala Ser
    50                  55                  60

Cys Phe Tyr Tyr Val Ala Thr Thr Tyr Phe Pro Leu Leu Pro His Pro
65                  70                  75                  80

Leu Ser Tyr Phe Ala Trp Pro Leu Tyr Trp Ala Cys Gln Gly Cys Val
                85                  90                  95

Leu Thr Gly Val
            100
```

<210> SEQ ID NO 9
<211> LENGTH: 283
<212> TYPE: PRT
<213> ORGANISM: Brassica juncea

<400> SEQUENCE: 9

```
Val Ile Ala His Glu Cys Gly His His Ala Phe Ser Asp Tyr Gln Trp
1               5                   10                  15

Leu Asp Asp Thr Val Gly Leu Ile Phe His Ser Phe Leu Leu Val Pro
                20                  25                  30

Tyr Phe Ser Trp Lys Tyr Ser His Arg Arg His Ser Asn Thr Gly
            35                  40                  45

Ser Leu Glu Arg Asp Glu Val Phe Val Pro Lys Lys Ser Asp Ile
    50                  55                  60

Lys Trp Tyr Gly Lys Tyr Leu Asn Asn Pro Leu Gly Arg Thr Val Met
65                  70                  75                  80

Leu Thr Val Gln Phe Thr Leu Gly Trp Pro Leu Tyr Leu Ala Phe Asn
                85                  90                  95

Val Ser Gly Arg Pro Tyr Asp Gly Gly Phe Ala Cys His Phe His Pro
            100                 105                 110

Asn Ala Pro Ile Tyr Asn Asp Arg Glu Arg Leu Gln Ile Tyr Ile Ser
            115                 120                 125

Asp Ala Gly Ile Leu Ala Val Cys Tyr Gly Leu Tyr Arg Tyr Ala Ala
        130                 135                 140

Val Gln Gly Val Ala Ser Met Val Cys Phe Tyr Gly Val Pro Leu Leu
145                 150                 155                 160

Ile Val Asn Gly Phe Leu Val Leu Ile Thr Tyr Leu Gln His Thr His
                165                 170                 175

Pro Ser Leu Pro His Tyr Asp Ser Ser Glu Trp Asp Trp Leu Arg Gly
            180                 185                 190

Ala Leu Ala Thr Val Asp Arg Asp Tyr Gly Ile Leu Asn Lys Val Phe
        195                 200                 205

His Asn Ile Thr Asp Thr His Val Ala His His Leu Phe Ser Thr Met
    210                 215                 220

Pro His Tyr His Ala Met Glu Ala Thr Lys Ala Ile Lys Pro Ile Leu
225                 230                 235                 240

Gly Glu Tyr Tyr Gln Phe Asp Gly Thr Pro Val Val Lys Ala Met Trp
                245                 250                 255
```

```
                                    -continued
Arg Glu Ala Lys Glu Cys Ile Tyr Val Glu Pro Asp Arg Gln Gly Glu
            260                 265                 270

Lys Lys Gly Val Phe Trp Tyr Asn Asn Lys Leu
            275                 280
```